US009669091B2

(12) United States Patent
Weiner et al.

(10) Patent No.: US 9,669,091 B2
(45) Date of Patent: Jun. 6, 2017

(54) VACCINES HAVING AN ANTIGEN AND INTERLEUKIN-23 AS AN ADJUVANT

(71) Applicants: David B. Weiner, Merion, PA (US); Jian Yan, Haverford, PA (US); Matthew Morrow, Bala Cynwyd, PA (US); Bernadette Ferraro, Philadelphia, PA (US); David Hokey, Rockville, MD (US)

(72) Inventors: David B. Weiner, Merion, PA (US); Jian Yan, Haverford, PA (US); Matthew Morrow, Bala Cynwyd, PA (US); Bernadette Ferraro, Philadelphia, PA (US); David Hokey, Rockville, MD (US)

(73) Assignees: INOVIO PHARMACEUTICALS, INC., Blue Bell, PA (US); THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 14/775,087

(22) PCT Filed: Mar. 13, 2014

(86) PCT No.: PCT/US2014/025348
§ 371 (c)(1),
(2) Date: Sep. 11, 2015

(87) PCT Pub. No.: WO2014/151279
PCT Pub. Date: Sep. 25, 2014

(65) Prior Publication Data
US 2016/0030557 A1 Feb. 4, 2016

Related U.S. Application Data

(60) Provisional application No. 61/788,942, filed on Mar. 15, 2013.

(51) Int. Cl.
*C12P 21/02* (2006.01)
*C12N 15/03* (2006.01)
*A61K 39/39* (2006.01)
*C07K 14/54* (2006.01)
*A61K 9/00* (2006.01)
*A61K 39/015* (2006.01)
*A61K 39/12* (2006.01)
*C12N 7/00* (2006.01)
*C12P 21/00* (2006.01)
*C12N 15/09* (2006.01)
*C12N 15/10* (2006.01)
*A61K 39/00* (2006.01)

(52) U.S. Cl.
CPC ............ *A61K 39/39* (2013.01); *A61K 9/0009* (2013.01); *A61K 39/015* (2013.01); *A61K 39/12* (2013.01); *C07K 14/54* (2013.01); *C12N 7/00* (2013.01); *C12N 15/03* (2013.01); *C12P 21/02* (2013.01); *A61K 2039/53* (2013.01); *A61K 2039/54* (2013.01); *A61K 2039/55527* (2013.01); *C12N 2710/20033* (2013.01); *C12N 2710/20034* (2013.01)

(58) Field of Classification Search
None
See application file for complete search history.

(56) References Cited

U.S. PATENT DOCUMENTS

2007/0048261 A1  3/2007  Mettens et al.
2008/0260765 A1  10/2008  Wu et al.
2012/0107268 A1  5/2012  Abraham et al.

FOREIGN PATENT DOCUMENTS

WO  03/084467 A2   10/2003
WO  WO 2005/108425  * 11/2005
WO  2013/090296 A1  6/2013

OTHER PUBLICATIONS

Matsui et al, Journal of Virology, 2004; vol. 78, No. 17, pp. 9093-9104.*
Ha et al, The Journal of Immunology, 2004; vol. 172, pp. 525-531.*
Wozniak et al, Infection and Immunity, 2006; vol. 74, No. 1, pp. 557-565.*
Ferraro et al, Clinical Infectious Diseases; 2011; vol. 53, No. 3, pp. 296-302.*
Guan I et al, Molecular medicine, 2011, vol. 17, No. 7-8, pp. 646-656.*
Guan II et al, Immunotherapy, Dec. 2013, vol. 5, No. 12, pp. 1313-1322.*
Overwijk et al., "Immunological and Antitumor Effects of IL-23 as a Cancer Vaccine Adjuvant", The Journal of Immunology, vol. 176, No. 9, pp. 5231-5222 (May 1, 2006).
Williman et al., "The use of Th1 cytokines, IL-12 and IL-23, to modulate the immune response raised to a DNA vaccine delivered by gene gun", Vaccine, vol. 24, No. 21, pp. 4471-4474(May 22, 2006).
Matsui et al., "Adjuvant Activities of Novel Cytokines, Interleukin-23 (IL-23) and IL-27, for Induction of Hepatitis C Virus-Specific Cytotoxic T Lymphocytes in HLA-A*0201 Transgenic Mice", Journal of Virology., vol. 78, No. 17, pp. 9093-9104 (Aug. 12, 2004).
Wozniak et al., "Plasmid Interleukin-23 (IL-23), but Not Plasmid IL-27, Enhances the Protective Efficacy of a DNA Vaccine against Mycobacterium tuberculosis Infection", Infection and Immunity, vol. 74, No. 1, pp. 557-565 (Jan. 1, 2006).
Jalah et al., "The p40 Subunit of Interleukin (IL)-12 Promotes Stabilization and Export of the p35 Subunit: Implications for Improved IL-12 Cytokine Production", Journal of Biological Chemistry, vol. 288, No. 9, pp. 6763-6776 (Mar. 1, 2013).
Gothelf et al., "What you always needed to know about electroporation based DNA vaccines", Human Vaccines & Immunotherapeutics, vol. 8, No. 11, pp. 1694-1702 (Nov. 24, 2012).

(Continued)

Primary Examiner — Joanne Hama
Assistant Examiner — Fozia Hamud
(74) Attorney, Agent, or Firm — Riverside Law LLP

(57) ABSTRACT

Disclosed herein is a vaccine comprising an antigen and IL-23. Also disclosed herein are methods for increasing an immune response in a subject. The methods may comprise administering the vaccine to the subject in need thereof.

22 Claims, 5 Drawing Sheets

(56) References Cited

OTHER PUBLICATIONS

Ohlschlager et al., "Enhancement of immunogenicity of a therapeutic cervical cancer DNA-based vaccine by co-application of sequence-optimized genetic adjuvants", International Journal of Cancer, vol. 125, No. 1, pp. 189-198 (Jul. 1, 2009).

\* cited by examiner

Optimized Nucleic Acid Sequence Encoding the p19 Subunit of Human IL-23

ATGCTGGGGTCAAGAGCCGTGATGCTGCTGCTGCTGCTGCCTTGGACTGCACAGGGCCGAGCCGTGCC
AGGAGGGTCTAGTCCCGCTTGGACTCAGTGCCAGCAGCTGTCTCAGAAGCTGTGCACCCTGGCCTGGAG
TGCTCACCCACTGGTGGGGCATATGGACCTGCGAGAGGAAGGAGATGAGGAAACCACAAACGACGTGC
CTCACATCCAGTGCGGCGACGGGTGTGATCCACAGGGACTGAGGGATAATTCCCAGTTCTGCCTGCAGC
GCATCCATCAGGGCCTGATTTTCTACGAGAAGCTGCTGGGAAGCGATATCTTCACCGGCGAACCCAGTC
TGCTGCCAGACTCACCTGTGGGACAGCTGCACGCAAGCCTGCTGGGACTGTCCCAGCTGCTGCAGCCAG
AGGGGCACCATTGGGAAACCCAGCAGATCCCTAGCCTGTCCCCATCTCAGCCATGGCAGCGGCTGCTGC
TGCGGTTCAAGATTCTGAGATCTCTGCAGGCATTCGTCGCTGTCGCCGCAAGGGTCTTCGCACACGGAG
CCGCAACACTGTCCCCA (SEQ ID NO:22)

FIG. 7A

Optimized Nucleic Acid Sequence Encoding the p40 Subunit of Human IL-23

ATGTGCCATCAGCAGCTGGTCATCTCTTGGTTTAGTCTGGTGTTTCTGGCTTCTCCACTGGTCGCTATCTG
GGAACTGAAAAAGGATGTGTACGTGGTCGAGCTGGACTGGTATCCAGATGCACCCGGAGAAATGGTGG
TCCTGACCTGCGACACACCCGAGGAAGATGGCATCACTTGGACCCTGGACCAGAGCTCCGAGGTGCTG
GGATCTGGCAAGACACTGACTATTCAGGTCAAAGAATTCGGGGATGCCGGACAGTACACATGTCACAA
GGGCGGGGAGGTGCTGAGTCACTCACTGCTGCTGCTGCATAAGAAAGAAGACGGCATCTGGTCTACTG
ACATTCTGAAGGATCAGAAAGAGCCTAAGAACAAAACCTTCCTGAGATGCGAAGCTAAGAATTATAGTG
GGAGGTTTACCTGTTGGTGGCTGACCACAATCTCAACTGACCTGACCTTTAGCGTGAAATCTAGTAGGG
GGTCAAGCGATCCACAGGGAGTGACCTGCGGAGCAGCTACACTGAGCGCCGAGCGGGTGAGAGGAGA
CAACAAGGAGTACGAATATAGTGTCGAGTGCCAGGAAGATTCAGCCTGTCCCGCAGCCGAGGAATCCC
TGCCTATCGAAGTGATGGTGGACGCTGTGCACAAGCTGAAATACGAAAACTACACATCCTCTTTCTTTAT
TCGCGACATCATTAAGCCAGATCCCCCTAAAAACCTGCAGCTGAAGCCCCTGAAAAATTCCCGACAGGT
GGAGGTCTCTTGGGAATACCCTGATACATGGAGCACTCCACATTCTTATTTCAGTCTGACTTTTTGCGTGC
AGGTCCAGGGCAAGAGCAAAAGGGAGAAGAAAGACCGCGTGTTCACCGATAAGACATCCGCTACTGTC
ATCTGTCGAAAAAACGCAAGCATTTCCGTGCGGGCACAGGATAGGTATTATTCCAGCAGTTGGTCTGAG
TGGGCTTCCGTCCCTTGTAGTTGA (SEQ ID NO:23)

FIG. 7B

SEQUENCE LISTING

```
<160> NUMBER OF SEQ ID NOS: 23

<210> SEQ ID NO 1
<211> LENGTH: 588
<212> TYPE: DNA
```

<213> ORGANISM: Mus musculus

<400> SEQUENCE: 1

```
atgctggatt gcagagcagt aataatgcta tggctgttgc cctgggtcac tcagggcctg      60
gctgtgccta ggagtagcag tcctgactgg gctcagtgcc agcagctctc tcggaatctc     120
tgcatgctag cctggaacgc acatgcacca gcgggacata tgaatctact aagagaagaa     180
gaggatgaag agactaaaaa taatgtgccc cgtatccagt gtgaagatgg ttgtgaccca     240
caaggactca aggacaacag ccagttctgc ttgcaaagga tccgccaagg tctggctttt     300
tataagcacc tgcttgactc tgacatcttc aaaggggagc ctgctctact ccctgatagc     360
cccatggagc aacttcacac ctccctacta ggactcagcc aactcctcca gccagaggat     420
cacccccggg agacccaaca gatgcccagc ctgagttcta gtcagcagtg gcagcgcccc     480
cttctccgtt ccaagatcct tcgaagcctc caggcctttt tggccatagc tgcccgggtc     540
tttgcccacg gagcagcaac tctgactgag cccttagtgc aacagct               588
```

<210> SEQ ID NO 2
<211> LENGTH: 196
<212> TYPE: PRT
<213> ORGANISM: Mus musculus

<400> SEQUENCE: 2

```
Met Leu Asp Cys Arg Ala Val Ile Met Leu Trp Leu Leu Pro Trp Val
 1               5                  10                  15

Thr Gln Gly Leu Ala Val Pro Arg Ser Ser Pro Asp Trp Ala Gln
            20                  25                  30

Cys Gln Gln Leu Ser Arg Asn Leu Cys Met Leu Ala Trp Asn Ala His
        35                  40                  45

Ala Pro Ala Gly His Met Asn Leu Leu Arg Glu Glu Asp Glu Glu
    50                  55                  60

Thr Lys Asn Asn Val Pro Arg Ile Gln Cys Glu Asp Gly Cys Asp Pro
65                  70                  75                  80

Gln Gly Leu Lys Asp Asn Ser Gln Phe Cys Leu Gln Arg Ile Arg Gln
                85                  90                  95

Gly Leu Ala Phe Tyr Lys His Leu Leu Asp Ser Asp Ile Phe Lys Gly
            100                 105                 110

Glu Pro Ala Leu Leu Pro Asp Ser Pro Met Glu Gln Leu His Thr Ser
        115                 120                 125

Leu Leu Gly Leu Ser Gln Leu Leu Gln Pro Glu Asp His Pro Arg Glu
    130                 135                 140

Thr Gln Gln Met Pro Ser Leu Ser Ser Ser Gln Gln Trp Gln Arg Pro
145                 150                 155                 160

Leu Leu Arg Ser Lys Ile Leu Arg Ser Leu Gln Ala Phe Leu Ala Ile
                165                 170                 175

Ala Ala Arg Val Phe Ala His Gly Ala Ala Thr Leu Thr Glu Pro Leu
            180                 185                 190

Val Pro Thr Ala
        195
```

<210> SEQ ID NO 3
<211> LENGTH: 567
<212> TYPE: DNA
<213> ORGANISM: Macaca mulatta

<400> SEQUENCE: 3

| | |
|---|---|
| atgctgggga gcagagctgt aatgctgctg ttgctgctgt cctggacagc tcagggcagg | 60 |
| gctgtgcctg ggggcagcag ccctgcctgg gctcagtgcc agcagctttc acagaagctc | 120 |
| tgcacactgg cctggagtgc acatccacta gtgggacaca tggatctaag agaagaggga | 180 |
| gatgaagaga ctacaaatga tgttccccat atccagtgtg gagatggctg tgacccccaa | 240 |
| ggactcaggg acaacagtca gttctgcttg caaaggattc gccagggtct gattttttac | 300 |
| gagaagctac tgggatcgga tatttttcaca ggggagcctt ctctgctgcc tgatagccct | 360 |
| gtgggccagc ttcatgcctc cctactgggc tcagccaac tcctgcagcc tgagggtcac | 420 |
| cactgggaga ctcagcagat tccaagcccc agtcccagcc agccatggca gcgcctcctt | 480 |
| ctccgcttca aaatccttcg cagcctccag gcctttgtgg ctgtagctgc ccgggtcttt | 540 |
| gcccatggag cagcaaccct gagcccc | 567 |

<210> SEQ ID NO 4
<211> LENGTH: 189
<212> TYPE: PRT
<213> ORGANISM: Macaca mulatta

<400> SEQUENCE: 4

Met Leu Gly Ser Arg Ala Val Met Leu Leu Leu Leu Ser Trp Thr
1               5                   10                  15

Ala Gln Gly Arg Ala Val Pro Gly Ser Ser Pro Ala Trp Ala Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile Arg Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
130                 135                 140

Gln Gln Ile Pro Ser Pro Ser Pro Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

<210> SEQ ID NO 5
<211> LENGTH: 567
<212> TYPE: DNA
<213> ORGANISM: Homo sapiens

<400> SEQUENCE: 5

| | |
|---|---|
| atgctgggga gcagagctgt aatgctgctg ttgctgctgc cctggacagc tcagggcaga | 60 |
| gctgtgcctg ggggcagcag ccctgcctgg actcagtgcc agcagctttc acagaagctc | 120 |
| tgcacactgg cctggagtgc acatccacta gtgggacaca tggatctaag agaagaggga | 180 |
| gatgaagaga ctacaaatga tgttccccat atccagtgtg gagatggctg tgacccccaa | 240 |

```
ggactcaggg acaacagtca gttctgcttg caaaggatcc accagggtct gattttttat    300
gagaagctgc taggatcgga tattttcaca ggggagcctt ctctgctccc tgatagcccc    360
gtgggccagc ttcatgcctc cctactgggc ctcagccaac tcctgcagcc tgagggtcac    420
cactgggaga ctcagcagat tccaagcctc agtcccagcc agccatggca gcgtctcctt    480
ctccgcttca aaatccttcg cagcctccag gcctttgtgg ctgtagccgc ccgggtcttt    540
gcccatggag cagcaaccct gagtccc                                        567
```

<210> SEQ ID NO 6
<211> LENGTH: 189
<212> TYPE: PRT
<213> ORGANISM: Homo sapiens

<400> SEQUENCE: 6

```
Met Leu Gly Ser Arg Ala Val Met Leu Leu Leu Leu Pro Trp Thr
 1               5                  10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185
```

<210> SEQ ID NO 7
<211> LENGTH: 1005
<212> TYPE: DNA
<213> ORGANISM: Mus musculus

<400> SEQUENCE: 7

```
atgtgtcctc agaagctaac catctcctgg tttgccatcg ttttgctggt gtctccactc     60
atggccatgt gggagctgga gaaagacgtt tatgttgtag aggtggactg gactcccgat    120
gcccctggag aaacagtgaa cctcacctgt gacacgcctg aagaagatga catcacctgg    180
acctcagacc agagacatgg agtcataggc tctggaaaga ccctgaccat cactgtcaaa    240
gagtttctag atgctggcca gtacacctgc cacaaggagg cgagactct gagccactca    300 catctgctgc tccacaagaa ggaaaatgga atttggtcca ctgaaattt aaaaaatttc    360 aaaaacaaga ctttcctgaa gtgtgaagca ccaaattact ccggacggtt cacgtgctca    420
```

```
tggctggtgc aaagaaacat ggacttgaag ttcaacatca agagcagtag cagttcccct      480
gactctcggg cagtgacatg tggaatggcg tctctgtctg cagagaaggt cacactggac      540
caaagggact atgagaagta ttcagtgtcc tgccaggagg atgtcacctg cccaactgcc      600
gaggagaccc tgcccattga actggcgttg gaagcacggc agcagaataa atatgagaac      660
tacagcacca gcttcttcat cagggacatc atcaaaccag acccgcccaa gaacttgcag      720
atgaagcctt tgaagaactc acaggtggag gtcagctggg agtaccctga ctcctggagc      780
actccccatt cctacttctc cctcaagttc tttgttcgaa tccagcgcaa gaaagaaaag      840
atgaaggaga cagaggaggg gtgtaaccag aaaggtgcgt tcctcgtaga agaagacatct      900 accgaagtcc aatgcaaagg cgggaatgtc tgcgtgcaag ctcaggatcg ctattacaat      960
tcctcatgca gcaagtgggc atgtgttccc tgcagggtcc gatcc                      1005
```

<210> SEQ ID NO 8
<211> LENGTH: 335
<212> TYPE: PRT
<213> ORGANISM: Mus musculus

<400> SEQUENCE: 8

```
Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Ile Thr Trp Thr Ser Asp Gln
50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270
```

```
Arg Ile Gln Arg Lys Lys Glu Lys Met Lys Glu Thr Glu Glu Gly Cys
            275                 280                 285
Asn Gln Lys Gly Ala Phe Leu Val Glu Lys Thr Ser Thr Glu Val Gln
            290                 295                 300
Cys Lys Gly Gly Asn Val Cys Val Gln Ala Gln Asp Arg Tyr Tyr Asn
305                 310                 315                 320
Ser Ser Cys Ser Lys Trp Ala Cys Val Pro Cys Arg Val Arg Ser
                325                 330                 335

<210> SEQ ID NO 9
<211> LENGTH: 984
<212> TYPE: DNA
<213> ORGANISM: Macaca mulatta

<400> SEQUENCE: 9
atgtgtcacc agcagctggt catctcttgg ttttccctgg tttttctggc atctcccctc       60
atggccatat gggaactgaa gaaagacgtt tatgttgtag aattggactg gtacccggat      120 gccccctggag aaatggtggt cctcacctgt gacacccctg aagaagatgg tatcacctgg     180
accttggacc agagtggtga ggtcttaggc tctggcaaaa ccctgaccat ccaagtcaaa      240
gagtttggag atgctggcca gtacacctgt cacaaaggag cgaggctct aagccattca       300 ctcctgctgc ttcacaaaaa ggaagatgga atttggtcca ctgatgtttt aaaggaccag      360
aaagaaccca aaataagac cttctctaaga tgtgaggcca aaaattattc tggacgtttc      420
acctgctggt ggctgacgac aatcagtact gatctgacat tcagtgtcaa agcagcaga      480 ggctcttcta ccccaagg ggtgacgtgt ggagccgtta cactctctgc agagagggtc       540
agaggggaca taaggagta tgagtactca gtggagtgcc aggaggacag tgcctgccca      600 gccgctgagag agaggctgcc cattgaggtc atggtggatg ccattcacaa gctcaagtat    660
gaaaactaca ccagcagctt cttcatcagg gacatcatca acccgaccc acccaagaac     720 ttgcagctga agccattaaa gaattctcgg caggtgagg tcagctggga gtaccctgac      780
acctggagta ctccacattc ctacttctcc ctgacattct gcatccaggt ccagggcaag    840
agcaagagag aaaagaaaga tagaatcttc acagacaaga cctcagccac ggtcatctgc     900
cgcaaaaatg ccagctttag cgtgcaggcc caggaccgct actatagctc atcttggagc    960
gaatgggcat ctgtgccctg cagt                                            984

<210> SEQ ID NO 10
<211> LENGTH: 328
<212> TYPE: PRT
<213> ORGANISM: Macaca mulatta

<400> SEQUENCE: 10

Met Cys His Gln Gln Leu Val Ile Ser Trp Phe Ser Leu Val Phe Leu
1               5                  10                  15
Ala Ser Pro Leu Met Ala Ile Trp Glu Leu Lys Lys Asp Val Tyr Val
            20                  25                  30
Val Glu Leu Asp Trp Tyr Pro Asp Ala Pro Gly Glu Met Val Val Leu
        35                  40                  45
Thr Cys Asp Thr Pro Glu Glu Asp Gly Ile Thr Trp Thr Leu Asp Gln
    50                  55                  60
Ser Gly Glu Val Leu Gly Ser Gly Lys Thr Leu Thr Ile Gln Val Lys
65                  70                  75                  80
Glu Phe Gly Asp Ala Gly Gln Tyr Thr Cys His Lys Gly Gly Glu Ala
                85                  90                  95
```

Leu Ser His Ser Leu Leu Leu His Lys Lys Glu Asp Gly Ile Trp
            100                 105                 110

Ser Thr Asp Val Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asn Pro Gln Gly Val Thr Cys Gly Ala Val Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Arg Leu Pro Ile
            195                 200                 205

Glu Val Met Val Asp Ala Ile His Lys Leu Lys Tyr Glu Asn Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Ile Gln Val Gln Gly Lys Ser Lys Arg Glu Lys Lys Asp Arg
            275                 280                 285

Ile Phe Thr Asp Lys Thr Ser Ala Thr Val Ile Cys Arg Lys Asn Ala
290                 295                 300

Ser Phe Ser Val Gln Ala Gln Asp Arg Tyr Tyr Ser Ser Ser Trp Ser
305                 310                 315                 320

Glu Trp Ala Ser Val Pro Cys Ser
                325

<210> SEQ ID NO 11
<211> LENGTH: 984
<212> TYPE: DNA
<213> ORGANISM: Homo sapiens

<400> SEQUENCE: 11
atgtgtcacc agcagttggt catctcttgg ttttccctgg tttttctggc atctcccctc    60
gtggccatat gggaactgaa gaaagatgtt tatgtcgtag aattggattg gtatccggat   120
gcccctggag aaatggtggt cctcacctgt gacacccctg aagaagatgg tatcacctgg   180
accttggacc agagcagtga ggtcttaggc tctggcaaaa ccctgaccat ccaagtcaaa   240
gagtttggag atgctggcca gtacacctgt cacaaaggag gcgaggttct aagccattcg   300
ctcctgctgc ttcacaaaaa ggaagatgga atttggtcca ctgatatttt aaaggaccag   360
aaagaaccca aaataagac ctttctaaga tgcgaggcca agaattattc tggacgtttc   420
acctgctggt ggctgacgac aatcagtact gatttgacat tcagtgtcaa agcagcaga   480 ggctcttctg accccaagg ggtgacgtgc ggagctgcta cactctctgc agagagagtc   540 agagggaca acaaggagta tgagtactca gtggagtgcc aggaggacag tgcctgccca   600
gctgctgagg agagtctgcc cattgaggtc atggtggatg ccgttcacaa gctcaagtat   660
gaaaactaca ccagcagctt cttcatcagg gacatcatca aacctgaccc acccaagaac   720
ttgcagctga agccattaaa gaattctcgg caggtggagg tcagctggga gtaccctgac   780

```
acctggagta ctccacattc ctacttctcc ctgacattct gcgttcaggt ccagggcaag      840
agcaagagag aaaagaaaga tagagtcttc acgacaagaa cctcagccac ggtcatctgc      900
cgcaaaaatg ccagcattag cgtgcgggcc caggaccgct actatagctc atcttggagc      960
gaatgggcat ctgtgccctg cagt                                             984
```

```
<210> SEQ ID NO 12
<211> LENGTH: 328
<212> TYPE: PRT
<213> ORGANISM: Homo sapiens

<400> SEQUENCE: 12

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325
```

<210> SEQ ID NO 13
<211> LENGTH: 6308
<212> TYPE: DNA
<213> ORGANISM: Artificial Sequence
<220> FEATURE:
<223> OTHER INFORMATION: plasmid WLV009-mIL-23 Opt
<220> FEATURE:
<221> NAME/KEY: misc_feature
<222> LOCATION: (299)..(1058)
<223> OTHER INFORMATION: Kanamycin
<220> FEATURE:
<221> NAME/KEY: misc_feature
<222> LOCATION: (1228)..(1901)
<223> OTHER INFORMATION: pUC Ori
<220> FEATURE:
<221> NAME/KEY: misc_feature
<222> LOCATION: (2313)..(2519)
<223> OTHER INFORMATION: BGH PolyA
<220> FEATURE:
<221> NAME/KEY: misc_feature
<222> LOCATION: (2549)..(3199)
<223> OTHER INFORMATION: mIL-23p19 Opt
<220> FEATURE:
<221> NAME/KEY: misc_feature
<222> LOCATION: (3201)..(3709)
<223> OTHER INFORMATION: sCMV
<220> FEATURE:
<221> NAME/KEY: misc_feature
<222> LOCATION: (4346)..(4933)
<223> OTHER INFORMATION: hCMV
<220> FEATURE:
<221> NAME/KEY: misc_feature
<222> LOCATION: (5034)..(6101)
<223> OTHER INFORMATION: mIL-23p40 Opt
<220> FEATURE:
<221> NAME/KEY: misc_feature
<222> LOCATION: (6103)..(6104)
<223> OTHER INFORMATION: SV40 PolyA

<400> SEQUENCE: 13

```
aaatggggc gctgaggtct gcctcgtgaa gaaggtgttg ctgactcata ccaggcctga     60
atcgccccat catccagcca gaaagtgagg gagccacggt tgatgagagc tttgttgtag    120
gtggaccagt tggtgatttt gaacttttgc tttgccacgg aacggtctgc gttgtcggga    180
agatgcgtga tctgatcctt caactcagca aaagttcgat ttattcaaca aagccgccgt    240
cccgtcaagt cagcgtaatg ctctgccagt gttacaacca attaaccaat tctgcgttca    300
aaatggtatg cgttttgaca catccactat atatccgtgt cgttctgtcc actcctgaat    360
cccattccag aaattctcta gcgattccag aagtttctca gagtcggaaa gttgaccaga    420
cattacgaac tggcacagat ggtcataacc tgaaggaaga tctgattgct taactgcttc    480
agttaagacc gacgcgctcg tcgtataaca gatgcgatga tgcagaccaa tcaacatggc    540
acctgccatt gctacctgta cagtcaagga tggtagaaat gttgtcggtc cttgcacacg    600
aatattacgc catttgcctg catattcaaa cagctcttct acgataaggg cacaaatcgc    660
atcgtggaac gtttgggctt ctaccgattt agcagtttga tacactttct ctaagtatcc    720
acctgaatca taaatcggca aaatagagaa aaattgacca tgtgtaagcg gccaatctga    780
ttccacctga gatgcataat ctagtagaat ctcttcgcta tcaaaattca cttccacctt    840
ccactcaccg gttgtccatt catggctgaa ctctgcttcc tctgttgaca tgacacacat    900
catctcaata tccgaatagg gcccatcagt ctgacgacca agagagccat aaacaccaat    960
agccttaaca tcatccccat atttatccaa tattcgttcc ttaatttcat gaacaatctt    1020
cattctttct tctctagtca ttattattgg tccgttcata acaccccttg tattactgtt    1080
```

-continued

```
tatgtaagca gacagtttta ttgttcatga tgatatattt ttatcttgtg caatgtaaca     1140
tcagagattt tgagacacaa cgtggctttc cccggcccat gaccaaaatc ccttaacgtg     1200
agttttcgtt ccactgagcg tcagacccg tagaaaagat caaaggatct tcttgagatc     1260
cttttttcct gcgcgtaatc tgctgcttgc aaacaaaaaa accaccgcta ccagcggtgg     1320
tttgtttgcc ggatcaagag ctaccaactc ttttccgaa ggtaactggc ttcagcagag     1380
cgcagatacc aaatactgtc cttctagtgt agccgtagtt aggccaccac ttcaagaact     1440
ctgtagcacc gcctacatac ctcgctctgc taatcctgtt accagtggct gctgccagtg     1500
gcgataagtc gtgtcttacc gggttggact caagacgata gttaccggat aaggcgcagc     1560
ggtcgggctg aacggggggt tcgtgcacac agcccagctt ggagcgaacg acctacaccg     1620
aactgagata cctacagcgt gagctatgag aaagcgccac gcttcccgaa gggagaaagg     1680
cggacaggta tccggtaagc ggcagggtcg gaacaggaga gcgcacgagg gagcttccag     1740
ggggaaacgc ctggtatctt tatagtcctg tcgggtttcg ccacctctga cttgagcgtc     1800
gatttttgtg atgctcgtca ggggggcgga gcctatggaa aaacgccagc aacgcggcct     1860
ttttacggtt cctggccttt tgctggcctt tgctcacat gttctttcct gcgttatccc     1920
ctgattctgt ggataaccgt attaccgcct ttgagtgagc tgataccgct cgccgcagcc     1980
gaacgaccga gcgcagcgag tcagtgagcg aggaagcgga agagcgcctg atgcggtatt     2040
ttctccttac gcatctgtgc ggtatttcac accgcatatg gtgcactctc agtacaatct     2100
gctctgatgc cgcatagtta agccagtatc tgctccctgc ttgtgtgttg gaggtcgctg     2160
agtagtgcgc gagcaaaatt taagctacaa caaggcaagg cttgaccgac aattgcatga     2220
agaatctgct tagggttagg cgttttgcgc tgcttcgcga tgtacgggcc agatatagcc     2280
gcggcatcga tgataattcg gcttatttaa attccccagc atgcctgcta ttgtcttccc     2340
aatcctcccc cttgctgtcc tgccccaccc cacccccag aatagaatga cacctactca     2400
gacaatgcga tgcaatttcc tcattttatt aggaaaggac agtgggagtg caccttcca     2460 gggtcaagga aggcacgggg gagggcaaa caacagatgg ctggcaacta aaggacagt     2520 cgaggctgat cagcgagctc ggcgcgcctc atcaggcggt gggcaccagg ggctcggtca     2580
gggtggcagc gccgtgggcg aacaccctgg cggcgatagc caggaaggcc tgcaggcttc     2640
tcaggatctt gcttctcagc aggggcctct gccactgctg gctgctgctc aggctgggca     2700
tctgctgtgt ctcccggggg tggtcctcgg gctgcagcag ctggctcagg cccagcaggc     2760
tggtgtgcag ctgctccatg gggctgtcgg gcagcagggc gggctcgccc ttgaagatgt     2820
cgctgtccag caggtgcttg tagaaagcca gaccctgcct gatcctctgc aggcagaact     2880
ggctgttgtc cttcaggccc tgagggtcgc agccgtcctc gcactggatc ctgggcacgt     2940
tgttctttgt ctcctcgtcc tcctcctctc tcagcaggtt catgtggccg cagggcgt      3000 gggcgttcca ggccagcatg cacaggtttc tggacagctg ctggcactga gcccaatcgg     3060
ggctgctgct tctgggcacg gccagtccct gggtgaccca aggcaggagc cacagcataa     3120
tcacggccct gcagtccagg ctgtgcaccc tagtggcagc agccaccaga aacaggatcc     3180
aggtccagtc catggtggcc tcgagtgggc caagtttaa acgctcctcc gacgtcccca     3240
ggcagaatgg cggttcccta acgagcatt gcttatatag acctcccatt aggcacgcct     3300
accgcccatt tacgtcaatg gaacgcccat ttcgtcatt gccctccc attgacgtca     3360 atggggatgt acttggcagc catcgcgggc catttaccgc cattgacgtc aatgggagta     3420
ctgccaatgt accctggcgt acttccaata gtaatgtact tgccaagtta ctattaatag     3480
```

```
atattgatgt actgccaagt gggccattta ccgtcattga cgtcaatagg gggcgtgaga    3540
acggatatga atgggcaatg agccatccca ttgacgtcaa tggtgggtgg tcctattgac    3600
gtcaatgggc attgagccag gcgggccatt taccgtaatt gacgtcaatg ggggaggcgc    3660
catatacgtc aataggaccg cccatatgac gtcaatagga agaccatgc taagccgaat    3720
tatcgcggct atctgagggg actagggtgt gtttaggcga aaagcggggc ttcggttgta    3780
cgcggttagg agtcccctca ggatatagta gtttcgcttt tgcataggga gggggaaatg    3840
tagtcttatg caatactctt gtagtcttgc aacatggtaa cgatgagtta gcaacatgcc    3900
ttacaaggag agaaaaagca ccgtgcatgc cgattggtgg aagtaaggtg gtacgatcgt    3960
gccttattag gaaggcaaca gacgggtctg acatggattg gacgaaccac tgaattccgc    4020
attgcagaga tattgtattt aagtgcctag ctcgatacaa taaacgccat ttgaccattc    4080
accacattgg tgtgcacctc caagcttcga ccaattctca tgtttgacag cttatcatcg    4140
cagatccggg caacgttgtt gccattgctg caggcgcaga actggtaggt atggaagatc    4200
tatacattga atcaatattg gcaattagcc atattagtca ttggttatat agcataaatc    4260
aatattggct attggccatt gcatacgttg tatctatatc ataatatgta catttatatt    4320
ggctcatgtc caatatgacc gccatgttga cattgattat tgactagtta ttaatagtaa    4380
tcaattacgg ggtcattagt tcatagccca tatatggagt tccgcgttac ataacttacg    4440
gtaaatggcc cgcctggctg accgcccaac gacccccgcc cattgacgtc aataatgacg    4500
tatgttccca tagtaacgcc aatagggact ttccattgac gtcaatgggt ggagtattta    4560
cggtaaactg cccacttggc agtacatcaa gtgtatcata tgccaagtcc gccccctatt    4620
gacgtcaatg acggtaaatg gcccgcctgg cattatgccc agtacatgac cttacgggac    4680
tttcctactt ggcagtacat ctacgtatta gtcatcgcta ttaccatggt gatgcggttt    4740
tggcagtaca tcaatgggcg tggatagcgg tttgactcac ggggatttcc aagtctccac    4800
cccattgacg tcaatgggag tttgttttgg caccaaaatc aacgggactt tccaaaatgt    4860
cgtaacaact ccgccccatt gacgcaaatg ggcggtaggc gtgtacggtg ggaggtctat    4920
ataagcagag ctcgtttagt gaaccgtcag atcgcctgga gacgccatcc acgctgtttt    4980
gacctccata gaagacaccg gaccgatcc agcctccgcg ggcgcgcgtc gacgccacca    5040
tggactggac ctggatcctg tttctggtgg ctgctgccac aagggtgcac agctgccccc    5100
agaagctgac catcagctgg ttcgccatcg tgctgctggt gtcccccctg atggccatgt    5160
gggagctgga aaggacgtg tacgtggtgg aggtggactg gacacccgac gcccctggcg    5220
agacagtgaa cctgacctgc gacacccccg aggaggacga catcacctgg accagcgacc    5280
agaggcacgg cgtgatcggc agcggcaaga ccctgaccat caccgtgaag gagtttctgg    5340
acgccggcca gtacacctgc cacaagggcg gcgagacact gagccacagc cacctgctgc    5400
tgcacaagaa ggaaacggc atctggtcca ccgagatcct gaagaacttc aagaacaaga    5460
ccttcctgaa gtgcgaggcc ccaactatt ctggccgctt cacatgctct ggctggtgc    5520
agaggaacat ggacctgaag ttcaacatca gagcagcag cagctccccc gacagcaggg    5580
ccgtgacctg cggcatggcc agcctgagcg ccgagaaggt gacctggac cagagggact    5640
acgagaagta cagcgtgagc tgccaggagg acgtcacctg ccctaccgcc gaggagacac    5700
tgcccatcga gctggccctg gaggccaggc agcagaacaa gtacgagaac tactctacca    5760
gcttcttcat ccgggacatc atcaagcccg accccccaa gaacctgcag atgaagcccc    5820
```

| | |
|---|---|
| tgaagaacag ccaggtggag gtgtcctggg agtaccctga cagctggtcc accccccaca | 5880 |
| gctacttcag cctgaagttc ttcgtgagga tccagaggaa gaaagaaaag atgaaggaga | 5940 |
| cagaggaggg ctgcaaccag aagggcgcct tcctggtcga aagaccagc accgaggtgc | 6000 |
| agtgcaaggg cggcaacgtg tgcgtgcagg cccaggacag gtactacaac agcagctgca | 6060 |
| gcaagtgggc ctgcgtgccc tgcagagtga gaagctgatg aacgcgtaaa aagatccaga | 6120 |
| catgataaga tacattgatg agtttggaca aaccacaact agaatgcagt gaaaaaaatg | 6180 |
| cttttatttgt gaaatttgtg atgctattgc tttatttgta accattataa gctgcaataa | 6240 |
| acaagttaac aacaacaatt gcattcattt tatgtttcag gttcagggggg aggtgtggga | 6300 |
| ggttttttt | 6308 |

<210> SEQ ID NO 14
<211> LENGTH: 1239
<212> TYPE: DNA
<213> ORGANISM: Artificial Sequence
<220> FEATURE:
<223> OTHER INFORMATION: Circumsporozoite (CS) Antigen

<400> SEQUENCE: 14

| | |
|---|---|
| atgatgcgga agctggctat cctgagcgtg tccagcttcc tgttcgtgga ggccctgttc | 60 |
| caagagtacc agtgctacgg cagcagcagc aacacaagag tgctgaacga gctgaactac | 120 |
| gacaacgccg gcaccaacct gtacaacgag ctggaaatga ctactacgg caagcaggaa | 180 |
| aactggtaca gcctgaagaa gaacagccgg tccctgggcg agaacgacga cggcaacaac | 240 |
| aacaacggcg acaacggcag agagggcaag gacgaggaca gcgggatgg caacaacgag | 300 |
| gacaacgaga gctgcggaa gcccaagcac aagaagctga gcagcccgg cgacggcaac | 360 |
| cccgaccca cgccaaccc caacgtggac cccaatgcca tcctaatgt cgatcccaac | 420 |
| gctaacccaa atgtcgaccc taacgcaaat cctaacgcca tcccaatgc aaaccctaat | 480 |
| gccaacccaa atgctaatcc aaacgcaaac cccaatgcta ccccaacgc taaccctaat | 540 |
| gcaaatccaa atgccaaccc caacgccaac ccaaacgcca tcccaacgc taatcctaac | 600 |
| gctaaccca acgccaatcc taacgccaac ccaaacgcta cccaaatgc caaccccaat | 660 |
| gcaaatccta atgctaatcc taacgctaat ccaaatgcaa atccaaacgc taatcctaat | 720 |
| gccaacccta acgcaaaccc caacgcaaat ccaaatgcta cccaaatgc aaatcccaac | 780 |
| gccaatccaa acgcaaatcc aaatgccaat cctaatgcaa accctaatgc aaatcccaat | 840 |
| gctaatccta atgctaatcc aaacaagaac accagggca acggccaggg ccacaacatg | 900 |
| cccaacgacc ccaaccggaa cgtggacgag aatgccaatg ccaacaacgc cgtgaagaac | 960 |
| aacaacaatg aggaacccag cgacaagcac atcgagcagt acctcaagaa gatccagaac | 1020 |
| agcctgagca ccgagtggag ccctgtagc gtgacctgcg gcaacggcat ccaagtccgg | 1080 |
| atcaagcccg gcagcgccaa caagcccaag gacgagctgg attacgagaa cgacatcgag | 1140 |
| aagaaaatct gcaagatgga aaagtgcagc agcgtgttca cgtggtcaa cagcagcatc | 1200 |
| ggcctgatca tggtgctgag ctttctgttc ctcaactga | 1239 |

<210> SEQ ID NO 15
<211> LENGTH: 412
<212> TYPE: PRT
<213> ORGANISM: Artificial Sequence
<220> FEATURE:
<223> OTHER INFORMATION: Circumsporozoite (CS) Antigen

<400> SEQUENCE: 15

```
Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Asn Thr
            20                  25                  30

Arg Val Leu Asn Glu Leu Asn Tyr Asp Asn Ala Gly Thr Asn Leu Tyr
                35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Asn Asn Gly Asp Asn Gly Arg Glu Gly Lys Asp Glu Asp Lys Arg Asp
                85                  90                  95

Gly Asn Asn Glu Asp Asn Glu Lys Leu Arg Lys Pro Lys His Lys Lys
                100                 105                 110

Leu Lys Gln Pro Gly Asp Gly Asn Pro Asp Pro Asn Ala Asn Pro Asn
            115                 120                 125

Val Asp Pro Asn Ala Asn Pro Asn Val Asp Pro Asn Ala Asn Pro Asn
    130                 135                 140

Val Asp Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
                180                 185                 190

Ala Asn Pro Asn Ala Asn Pro Asn Ala Asn Pro Asn Ala Asn Pro Asn
                195                 200                 205

Ala Asn Pro Asn Ala Asn Pro Asn Ala Asn Pro Asn Ala Asn Pro Asn
                210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Pro Asn Ala Asn Pro Asn Ala Asn Pro Asn
                260                 265                 270

Ala Asn Pro Asn Ala Asn Pro Asn Ala Asn Pro Asn Ala Asn Pro Asn
                275                 280                 285

Lys Asn Asn Gln Gly Asn Gly Gln Gly His Asn Met Pro Asn Asp Pro
            290                 295                 300

Asn Arg Asn Val Asp Glu Asn Ala Asn Ala Asn Ala Val Lys Asn
305                 310                 315                 320

Asn Asn Asn Glu Glu Pro Ser Asp Lys His Ile Glu Gln Tyr Leu Lys
                325                 330                 335

Lys Ile Gln Asn Ser Leu Ser Thr Glu Trp Ser Pro Cys Ser Val Thr
                340                 345                 350

Cys Gly Asn Gly Ile Gln Val Arg Ile Lys Pro Gly Ser Ala Asn Lys
                355                 360                 365

Pro Lys Asp Glu Leu Asp Tyr Glu Asn Asp Ile Glu Lys Lys Ile Cys
    370                 375                 380

Lys Met Glu Lys Cys Ser Ser Val Phe Asn Val Val Asn Ser Ser Ile
385                 390                 395                 400

Gly Leu Ile Met Val Leu Ser Phe Leu Phe Leu Asn
                405                 410
```

<210> SEQ ID NO 16
<211> LENGTH: 818
<212> TYPE: DNA
<213> ORGANISM: Artificial Sequence
<220> FEATURE:
<223> OTHER INFORMATION: HPV genotype 16 E6 and E7 Antigens
<220> FEATURE:
<221> NAME/KEY: misc_feature
<222> LOCATION: (13)..(66)
<223> OTHER INFORMATION: IgE leader

<400> SEQUENCE: 16

```
gaattcgcca ccatggactg gacctggatc ctgttcctgg tggccgccgc cacacgggtg    60
cacagcttcc aggacccca ggagagcggc agaaagctgc ctcagctgtg taccgagctg   120
cagaccacca tccacgacat catcctggag tgtgtgtact gtaagcagca gctgctgagg   180
agagaggtgt acgaccggga cctgtgtatc gtgtacaggg acggcaatcc ctacgccgtg   240
tgtgacaagt gcctgaagtt ctacagcaag atcagcgagt accggcacta ctgctacagc   300
ctgtacggca ccaccctgga gcagcagtac aacaagcccc tgtgtgacct gctgatccgg   360
tgtatcaact gccagaagcc cctgcagaga cacctggaca agaagcagcg gttccacaac   420
atcaggggca gatggaccgg cagatgtatg agctgctgcc ggagcagcag aaccagaagg   480
gagacccagc tgagaggccg aagagaaga agccacggcg ataccccac cctgcacgag   540
tacatgctgg acctgcagcc tgagaccacc gatctgtacg gctacggcca gctgaatgac   600
agcagcgagg aggaggatga gatcgacggc cctgccggcc aggccgagcc cgacagagcc   660
cactacaaca tcgtgacctt tgctgtaag tgtgacagca ccctgagact gtgcgtgcag   720
agcacccacg tggacatcag aacctggag gatctgctga tgggcacct gggcatcgtg   780
tgtcccatct gctcccagaa accctgatga gcggccgc                          818
```

<210> SEQ ID NO 17
<211> LENGTH: 264
<212> TYPE: PRT
<213> ORGANISM: Artificial Sequence
<220> FEATURE:
<223> OTHER INFORMATION: HPV genotype 16 E6 and E7 Antigens
<220> FEATURE:
<221> NAME/KEY: MISC_FEATURE
<222> LOCATION: (1)..(18)
<223> OTHER INFORMATION: IgE leader

<400> SEQUENCE: 17

```
Met Asp Trp Thr Trp Ile Leu Phe Leu Val Ala Ala Thr Arg Val
1               5                  10                  15

His Ser Phe Gln Asp Pro Gln Glu Ser Gly Arg Lys Leu Pro Gln Leu
                20                  25                  30

Cys Thr Glu Leu Gln Thr Thr Ile His Asp Ile Ile Leu Glu Cys Val
            35                  40                  45

Tyr Cys Lys Gln Gln Leu Leu Arg Arg Glu Val Tyr Asp Arg Asp Leu
        50                  55                  60

Cys Ile Val Tyr Arg Asp Gly Asn Pro Tyr Ala Val Cys Asp Lys Cys
65                  70                  75                  80

Leu Lys Phe Tyr Ser Lys Ile Ser Glu Tyr Arg His Tyr Cys Tyr Ser
                85                  90                  95

Leu Tyr Gly Thr Thr Leu Glu Gln Gln Tyr Asn Lys Pro Leu Cys Asp
            100                 105                 110

Leu Leu Ile Arg Cys Ile Asn Cys Gln Lys Pro Leu Gln Arg His Leu
        115                 120                 125
```

```
Asp Lys Lys Gln Arg Phe His Asn Ile Arg Gly Arg Trp Thr Gly Arg
        130                 135                 140
Cys Met Ser Cys Cys Arg Ser Ser Arg Thr Arg Glu Thr Gln Leu
145                 150                 155                 160
Arg Gly Arg Lys Arg Ser His Gly Asp Thr Pro Thr Leu His Glu
                165                 170                 175
Tyr Met Leu Asp Leu Gln Pro Glu Thr Thr Asp Leu Tyr Gly Tyr Gly
                180                 185                 190
Gln Leu Asn Asp Ser Ser Glu Glu Asp Glu Ile Asp Gly Pro Ala
        195                 200                 205
Gly Gln Ala Glu Pro Asp Arg Ala His Tyr Asn Ile Val Thr Phe Cys
        210                 215                 220
Cys Lys Cys Asp Ser Thr Leu Arg Leu Cys Val Gln Ser Thr His Val
225                 230                 235                 240
Asp Ile Arg Thr Leu Glu Asp Leu Leu Met Gly Thr Leu Gly Ile Val
                245                 250                 255
Cys Pro Ile Cys Ser Gln Lys Pro
                260

<210> SEQ ID NO 18
<211> LENGTH: 651
<212> TYPE: DNA
<213> ORGANISM: Artificial Sequence
<220> FEATURE:
<223> OTHER INFORMATION: Sense sequence for mIL-23p19 Opt
<220> FEATURE:
<221> NAME/KEY: misc_feature
<222> LOCATION: (1)..(6)
<223> OTHER INFORMATION: Kozak Sequence
<220> FEATURE:
<221> NAME/KEY: misc_feature
<222> LOCATION: (7)..(60)
<223> OTHER INFORMATION: Coding sequence for IgE leader

<400> SEQUENCE: 18
gccaccatgg actggacctg atcctgtttt ctggtggctg ctgccactag gtgcacagc    60
ctggactgca gggccgtgat tatgctgtgg ctcctgcctt gggtcaccca gggactggcc   120
gtgcccagaa gcagcagccc cgattgggct cagtgccagc agctgtccag aaacctgtgc   180
atgctggcct ggaacgccca cgcccctgcc ggccacatga acctgctgag agaggaggag   240
gacgaggaga caaagaacaa cgtgcccagg atccagtgcg aggacggctg cgaccctcag   300
ggcctgaagg acaacagcca gttctgcctg cagaggatca ggcagggtct ggctttctac   360
aagcacctgc tggacagcga catcttcaag ggcgagcccg ccctgctgcc cgacagcccc   420
atggagcagc tgcacaccag cctgctgggc ctgagccagc tgctgcagcc cgaggaccac   480
ccccgggaga cacagcagat gcccagcctg agcagcagcc agcagtggca gaggcccctg   540
ctgagaagca agatcctgag aagcctgcag gccttcctgg ctatcgccgc agggtgttc    600
gcccacggcg ctgccaccct gaccgagccc ctggtgccca ccgcctgatg a             651

<210> SEQ ID NO 19
<211> LENGTH: 213
<212> TYPE: PRT
<213> ORGANISM: Artificial Sequence
<220> FEATURE:
<223> OTHER INFORMATION: Mouse IL-23 p19 with IgE leader
<220> FEATURE:
<221> NAME/KEY: MISC_FEATURE
<222> LOCATION: (1)..(18)
<223> OTHER INFORMATION: IgE Leader
```

<400> SEQUENCE: 19

Met Asp Trp Thr Trp Ile Leu Phe Leu Val Ala Ala Thr Arg Val
1               5                   10                  15

His Ser Leu Asp Cys Arg Ala Val Ile Met Leu Trp Leu Leu Pro Trp
            20                  25                  30

Val Thr Gln Gly Leu Ala Val Pro Arg Ser Ser Pro Asp Trp Ala
        35                  40                  45

Gln Cys Gln Gln Leu Ser Arg Asn Leu Cys Met Leu Ala Trp Asn Ala
    50                  55                  60

His Ala Pro Ala Gly His Met Asn Leu Leu Arg Glu Glu Asp Glu
65                  70                  75                  80

Glu Thr Lys Asn Asn Val Pro Arg Ile Gln Cys Glu Asp Gly Cys Asp
                85                  90                  95

Pro Gln Gly Leu Lys Asp Asn Ser Gln Phe Cys Leu Gln Arg Ile Arg
                100                 105                 110

Gln Gly Leu Ala Phe Tyr Lys His Leu Leu Asp Ser Asp Ile Phe Lys
            115                 120                 125

Gly Glu Pro Ala Leu Leu Pro Asp Ser Pro Met Glu Gln Leu His Thr
130                 135                 140

Ser Leu Leu Gly Leu Ser Gln Leu Leu Gln Pro Glu Asp His Pro Arg
145                 150                 155                 160

Glu Thr Gln Gln Met Pro Ser Leu Ser Ser Ser Gln Trp Gln Arg
                165                 170                 175

Pro Leu Leu Arg Ser Lys Ile Leu Arg Ser Leu Gln Ala Phe Leu Ala
            180                 185                 190

Ile Ala Ala Arg Val Phe Ala His Gly Ala Ala Thr Leu Thr Glu Pro
        195                 200                 205

Leu Val Pro Thr Ala
    210

<210> SEQ ID NO 20
<211> LENGTH: 1068
<212> TYPE: DNA
<213> ORGANISM: Artificial Sequence
<220> FEATURE:
<223> OTHER INFORMATION: Sense sequence for mIL-23p40 Opt
<220> FEATURE:
<221> NAME/KEY: misc_feature
<222> LOCATION: (1)..(6)
<223> OTHER INFORMATION: Kozak sequence
<220> FEATURE:
<221> NAME/KEY: misc_feature
<222> LOCATION: (7)..(60)
<223> OTHER INFORMATION: Coding sequence for IgE leader

<400> SEQUENCE: 20
gccaccatgg actggacctg datcctgttt ctggtggctg ctgccacaag ggtgcacagc        60
tgcccccaga agctgaccat cagctggttc gccatcgtgc tgctggtgtc ccccctgatg       120
gccatgtggg agctggagaa ggacgtgtac gtggtggagg tggactggac acccgacgcc       180
cctggcgaga cagtgaacct gacctgcgac accccggagg aggacgacat cacctggacc       240
agcgaccaga ggcacggcgt gatcggcagc ggcaagaccc tgaccatcac cgtgaaggag       300
tttctggacg ccggccagta cacctgccac aagggcggcg agacactgag ccacagccac       360
ctgctgctgc acaagaagga gaacggcatc tggtccaccg gatcctgaa gaacttcaag       420 aacaagacct tcctgaagtg cgaggccccc aactattctg gccgcttcac atgctcttgg       480

-continued

```
ctggtgcaga ggaacatgga cctgaagttc aacatcaaga gcagcagcag ctcccccgac      540
agcagggccg tgacctgcgg catggccagc ctgagcgccg agaaggtgac cctggaccag      600
agggactacg agaagtacag cgtgagctgc caggaggacg tcacctgccc taccgccgag      660
gagacactgc ccatcgagct ggccctggag gccaggcagc agaacaagta cgagaactac      720
tctaccagct tcttcatccg gacatcatc aagcccgacc ccccaagaa cctgcagatg        780
aagcccctga gaacagcca ggtggaggtg tcctgggagt accctgacag ctggtccacc       840
ccccacagct acttcagcct gaagttcttc gtgaggatcc agaggaagaa agaaaagatg      900
aaggagacag aggagggctg caaccagaag ggcgccttcc tggtcgaaaa gaccagcacc      960
gaggtgcagt gcaagggcgg caacgtgtgc gtgcaggccc aggacaggta ctacaacagc     1020
agctgcagca gtgggcctg cgtgccctgc agagtgagaa gctgatga                   1068
```

<210> SEQ ID NO 21
<211> LENGTH: 352
<212> TYPE: PRT
<213> ORGANISM: Artificial Sequence
<220> FEATURE:
<223> OTHER INFORMATION: Mouse IL-23 p40 with IgE leader
<220> FEATURE:
<221> NAME/KEY: MISC_FEATURE
<222> LOCATION: (1)..(18)
<223> OTHER INFORMATION: IgE Leader

<400> SEQUENCE: 21

```
Met Asp Trp Thr Trp Ile Leu Phe Leu Val Ala Ala Thr Arg Val
1               5                   10                  15

His Ser Cys Pro Gln Lys Leu Thr Ile Ser Trp Phe Ala Ile Val Leu
            20                  25                  30

Leu Val Ser Pro Leu Met Ala Met Trp Glu Leu Glu Lys Asp Val Tyr
        35                  40                  45

Val Val Glu Val Asp Trp Thr Pro Asp Ala Pro Gly Glu Thr Val Asn
    50                  55                  60

Leu Thr Cys Asp Thr Pro Glu Glu Asp Asp Ile Thr Trp Thr Ser Asp
65                  70                  75                  80

Gln Arg His Gly Val Ile Gly Ser Gly Lys Thr Leu Thr Ile Thr Val
                85                  90                  95

Lys Glu Phe Leu Asp Ala Gly Gln Tyr Thr Cys His Lys Gly Gly Glu
            100                 105                 110

Thr Leu Ser His Ser His Leu Leu Leu His Lys Lys Glu Asn Gly Ile
        115                 120                 125

Trp Ser Thr Glu Ile Leu Lys Asn Phe Lys Asn Lys Thr Phe Leu Lys
    130                 135                 140

Cys Glu Ala Pro Asn Tyr Ser Gly Arg Phe Thr Cys Ser Trp Leu Val
145                 150                 155                 160

Gln Arg Asn Met Asp Leu Lys Phe Asn Ile Lys Ser Ser Ser Ser Ser
                165                 170                 175

Pro Asp Ser Arg Ala Val Thr Cys Gly Met Ala Ser Leu Ser Ala Glu
            180                 185                 190

Lys Val Thr Leu Asp Gln Arg Asp Tyr Glu Lys Tyr Ser Val Ser Cys
        195                 200                 205

Gln Glu Asp Val Thr Cys Pro Thr Ala Glu Glu Thr Leu Pro Ile Glu
    210                 215                 220

Leu Ala Leu Glu Ala Arg Gln Gln Asn Lys Tyr Glu Asn Tyr Ser Thr
225                 230                 235                 240
```

```
Ser Phe Phe Ile Arg Asp Ile Ile Lys Pro Asp Pro Lys Asn Leu
                245                 250                 255
Gln Met Lys Pro Leu Lys Asn Ser Gln Val Glu Val Ser Trp Glu Tyr
            260                 265                 270
Pro Asp Ser Trp Ser Thr Pro His Ser Tyr Phe Ser Leu Lys Phe Phe
        275                 280                 285
Val Arg Ile Gln Arg Lys Lys Glu Lys Met Lys Glu Thr Glu Glu Gly
    290                 295                 300
Cys Asn Gln Lys Gly Ala Phe Leu Val Glu Lys Thr Ser Thr Glu Val
305                 310                 315                 320
Gln Cys Lys Gly Gly Asn Val Cys Val Gln Ala Gln Asp Arg Tyr Tyr
                325                 330                 335
Asn Ser Ser Cys Ser Lys Trp Ala Cys Val Pro Cys Arg Val Arg Ser
            340                 345                 350

<210> SEQ ID NO 22
<211> LENGTH: 567
<212> TYPE: DNA
<213> ORGANISM: Artificial Sequence
<220> FEATURE:
<223> OTHER INFORMATION: p19 optimized Human IL-23 DNA

<400> SEQUENCE: 22 atgctgggt caagagccgt gatgctgctg ctgctgctgc cttggactgc acagggccga      60
gccgtgccag gagggtctag tcccgcttgg actcagtgcc agcagctgtc tcagaagctg     120
tgcaccctgg cctggagtgc tcacccactg gtggggcata tggacctgcg agaggaagga     180
gatgaggaaa ccacaaacga cgtgcctcac atccagtgcg cgacgggtg tgatccacag      240 ggactgaggg ataattccca gttctgcctg cagcgcatcc atcagggcct gattttctac     300
gagaagctgc tgggaagcga tatcttcacc ggcgaaccca gtctgctgcc agactcacct     360
gtgggacagc tgcacgcaag cctgctggga ctgtcccagc tgctgcagcc agaggggcac     420
cattgggaaa cccagcagat ccctagcctg tccccatctc agccatggca gcggctgctg     480
ctgcggttca agattctgag atctctgcag gcattcgtcg ctgtcgccgc aagggtcttc     540
gcacacggag ccgcaacact gtcccca                                         567

<210> SEQ ID NO 23
<211> LENGTH: 987
<212> TYPE: DNA
<213> ORGANISM: Artificial Sequence
<220> FEATURE:
<223> OTHER INFORMATION: p40 optimized human IL-23

<400> SEQUENCE: 23
atgtgccatc agcagctggt catctcttgg tttagtctgg tgtttctggc ttctccactg      60
gtcgctatct gggaactgaa aaaggatgtg tacgtggtcg agctggactg gtatccagat     120
gcacccggag aaatggtggt cctgacctgc gacacacccg aggaagatgg catcacttgg     180
accctggacc agagctccga ggtgctggga tctggcaaga cactgactat tcaggtcaaa     240
gaattcgggg atgccggaca gtacacatgt cacaagggcg gggaggtgct gagtcactca     300
ctgctgctgc tgcataagaa agaagacggc atctggtcta ctgacattct gaaggatcag     360
aaagagccta agaacaaaac cttcctgaga tgcgaagcta agaattatag tgggaggttt     420
acctgttggt ggctgaccac aatctcaact gacctgacct ttagcgtgaa atctagtagg     480
gggtcaagcg atccacaggg agtgacctgc ggagcagcta cactgagcgc cgagcgggtg     540
```

```
agaggagaca acaaggagta cgaatatagt gtcgagtgcc aggaagattc agcctgtccc    600
gcagccgagg aatccctgcc tatcgaagtg atggtggacg ctgtgcacaa gctgaaatac    660
gaaaactaca catcctcttt ctttattcgc gacatcatta agccagatcc ccctaaaaac    720
ctgcagctga agcccctgaa aaattcccga caggtggagg tctcttggga ataccctgat    780
acatggagca ctccacattc ttatttcagt ctgacttttt gcgtgcaggt ccagggcaag    840
agcaaaaggg agaagaaaga ccgcgtgttc accgataaga catccgctac tgtcatctgt    900
cgaaaaaacg caagcatttc cgtgcgggca caggataggt attattccag cagttggtct    960
gagtgggctt ccgtcccttg tagttga                                        987
```

VACCINES HAVING AN ANTIGEN AND INTERLEUKIN-23 AS AN ADJUVANT

CROSS-REFERENCE TO RELATED APPLICATIONS

This application is the U.S. national stage application filed under 35 U.S.C. §371 claiming benefit to International Patent Application No. PCT/US14/025348, filed Mar. 13, 2014, which is entitled to priority under 35 U.S.C. §119(e) to U.S. Provisional Application No. 61/788,942, filed Mar. 15, 2013, each of which is hereby incorporated by reference in its entirety.

TECHNICAL FIELD

The present invention relates to vaccines comprising an antigen and IL-23, and methods of administering such vaccines.

BACKGROUND

Vaccines are used to stimulate an immune response in an individual to provide protection against and/or treatment for a particular disease. Some vaccines include an antigen to induce the immune response. Some antigens elicit a strong immune response while other antigens elicit a weak immune response. A weak immune response to an antigen can be strengthened by including an adjuvant in the vaccine. Adjuvants come in many different forms, for example, aluminum salts, oil emulsions, sterile constituents of bacteria or other pathogens, cytokines, and so forth.

Cytokines are proteins made by cells that affect the behavior of other cells, and unlike many adjuvants, can modulate specific immune responses. One such cytokine is the interleukin-23 (IL-23), which controls inflammation in peripheral tissues by directing amplification and stabilization of T helper type 17 (Th17) cell populations. Th17 cells produce the pro-inflammatory cytokine interleukin-17 (IL-17), and are distinct from Th1 cells, which produce the pro-inflammatory cytokine interferon-γ (IFN-γ) and are induced by IL-12. Th17 cells are also distinct from Th2 cells, which are induced by interleukin-4 (IL-4). Th17 cells are distinct from Th1 cells and Th2 cells because Th17 cells activate inflammatory responses in both adaptive and innate immunity while Th1 cells activate T cell responses in adaptive immunity and Th2 cells activate antibody production in adaptive immunity.

Vaccines are also administered in many different ways (e.g., injection, orally, etc.) into many different tissues (e.g., intramuscular, intradermal, etc.). Not all delivery methods, however, are equal. Some delivery methods allow for greater compliance within a population of individuals while other delivery methods may affect the immunogenicity and/or safety of the vaccine. Accordingly, a need remains in the art for the development of safe and more effective adjuvants that increase antigenic responses irrespective of the identity of the antigen and route of administration.

SUMMARY OF THE INVENTION

The present invention is directed to a vaccine comprising an antigen and IL-23. In the vaccine, a p19 subunit of IL-23 can be encoded by a nucleotide sequence as set forth in SEQ ID NO:22 and a p40 subunit of IL-23 can be encoded by a nucleotide sequence as set forth in SEQ ID NO:23.

In the vaccine, the antigen can be encoded by a first nucleic acid and IL-23 can be encoded by a second nucleic acid. The first and second nucleic acids of the vaccine may be expressed from an expression vector. The vaccine can further comprise an antigen peptide with the same encoded nucleic acid sequence as the above antigen and an IL-23 peptide with the same encoded nucleic acid sequence as the above IL-23. The antigen of the vaccine may comprise any antigen including, but not limited to, a viral, bacterial, fungal, mammalian, or parasite antigen. The antigen can be associated with an autoimmune disease, allergy, or asthma. The vaccine can further comprise a pharmaceutically acceptable excipient.

The present invention is also directed to a method for increasing an immune response in a subject, the method comprising administering the above vaccine to the subject in need thereof, wherein administering the vaccine includes at least one of intramuscular administration and intradermal administration. The vaccine can also be administered through electroporation. The increased immune response provided by the method can occur in at least one of a skin tissue and a muscle tissue of the subject. With the method, the immune response can be increased in the subject by about 75% to about 200%, about 90% to about 130%, or about 105%. Via the method, the immune response in the subject can be increased by at least about 3-fold or 1.5 fold. The method can further comprise altering recognition of at least one epitope in the antigen, wherein the at least one epitope in the antigen failed to be recognized by an immune system of a subject administered the antigen alone.

The present is also directed to a nucleic acid molecule comprising one or more nucleotide sequences selected from the group consisting of: SEQ ID NO:22, SEQ ID NO:23, a nucleotide sequence that is 95% identical or greater to SEQ ID NO:22, a nucleotide sequence that is 95% identical or greater to SEQ ID NO:23, and a combination thereof. The nucleic acid molecule can be a plasmid. The nucleic acid molecule can be one or more plasmids.

BRIEF DESCRIPTION OF THE DRAWINGS

FIGS. 7A and 7B show the optimized nucleotide sequences encoding the p19 subunit and p40 subunit, respectively, of human IL-23.

DETAILED DESCRIPTION

Figure 1A:
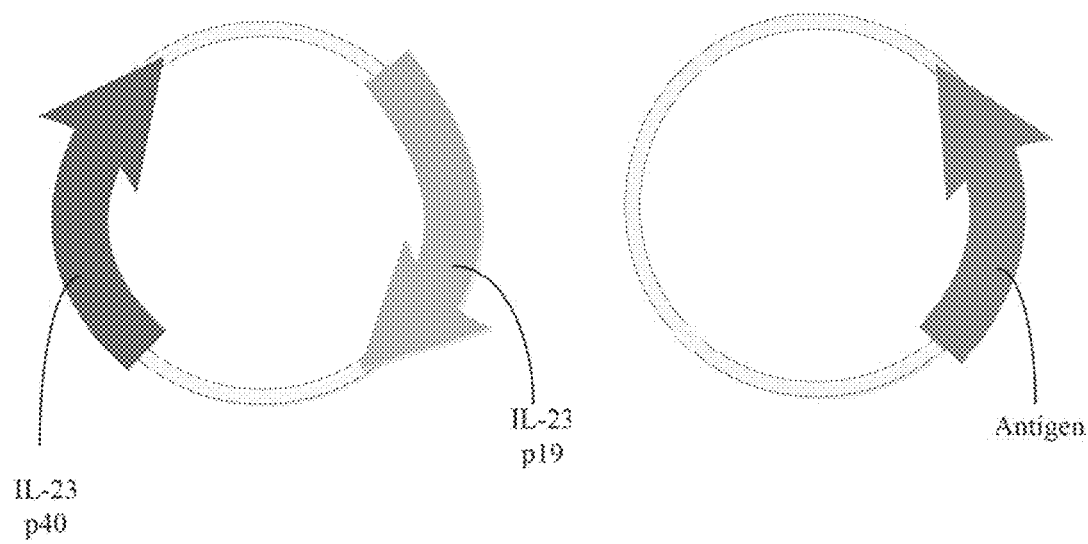
FIG. 1A and FIG. 1B show general maps of the IL-23 adjuvant constructs with an antigen on a different plasmid (FIG. 1A) and the same plasmid (FIG. 1B).

The present invention relates to vaccines that can be used to increase an immune response to an antigen in a subject by using IL-23 as an adjuvant. IL-23 can be a heterodimer of a p40 subunit and a p19 subunit, and, unlike the cytokine IL-12, can safely direct inflammatory responses in multiple tissues such as skin, muscle, etc.

In some instances, IL-23 can function as a universal adjuvant because a greater immune response is elicited in the subject regardless of the source of the antigen or the route of administration as compared to a vaccine comprising the antigen alone. IL-23 may further augment the immune response of both viral and parasite antigens, for example, a human papilloma virus (HPV) antigen and a *Plasmodium falciparum* antigen, respectively. In some instances, IL-23 can further augment the immune response in both muscle and skin tissues as demonstrated by increased interferon-γ (IFN-γ) production.

The vaccines of the present invention can also unexpectedly modify or alter epitope presentation to increase the immune response to the antigen. Such modification can be dependent upon IL-23. In some instances, IL-23 can direct the immune system to recognize new epitopes in the antigen, in addition to the epitopes recognized by the immune system in the absence of IL-23. In other instances, IL-23 can remap the landscape of epitope recognition by the immune system to increase the immune response to the antigen across tissues and irrespective of the antigen's identity or source.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein means any molecule added to the vaccines described herein to enhance the immunogenicity of the antigens.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means Watson-Crick (e.g., A-T/U and C-G) or Hoogsteen base pairing between nucleotides or nucleotide analogs of nucleic acid molecules.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" or "immunogenic fragment" as used herein means a nucleic acid sequence or a portion thereof that encodes a polypeptide capable of eliciting and/or increasing an immune response in a mammal. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below. In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, or at least 1000 nucleotides or more of at least one of the nucleic acid sequences set forth below.

Fragment or immunogenic fragment as used herein also means a polypeptide sequence or a portion thereof that is capable of eliciting and/or increasing an immune response in a mammal. The fragments can be polypeptide fragments selected from at least one of the various amino acid sequences set forth below. Fragments can comprise at least 10%, at least 20%, at least 30%, at least 40%, at least 50%, at least 60%, at least 70%, at least 80%, at least 90%, or at least 95% of one or more of the proteins set forth below. In some embodiments, fragments can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 190 amino acids or more, at least 200 amino acids or more, at least 210 amino acids or more, at least 220 amino acids or more, at least 230 amino acids or more, or at least 240 amino acids or more of at least one of the proteins set forth below.

"Genetic construct" or "construct" as used herein refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs or constructs that contain the necessary regulatory elements operably linked to a coding sequence that encodes a protein such that when present in the cell of the individual, the coding sequence will be expressed.

"Identical" or "identity" as used herein in the context of two or more nucleic acid or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of an antigen. The immune response can be in the form of a cellular or humoral immune response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to the cell, tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein or amino acid sequence set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus of the protein.

"Subject" as used herein can mean a mammal that wants to or is in need of being immunized with the herein described vaccines. The mammal can be a human, chimpanzee, dog, cat, horse, cow, mouse, or rat.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1%

SDS, incubating at 42° C., or, 5×SSC, 1% SDS, incubating at 65° C., with wash in 0.2×SSC, and 0.1% SDS at 65° C.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

"Substantially identical" as used herein can mean that a first and second amino acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more amino acids. Substantially identical can also mean that a first nucleic acid sequence and a second nucleic acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides.

"Treatment" or "treating" as used herein can mean protecting an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" as used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Variant can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof "Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid. The vector can contain or include one or more heterologous nucleic acid sequences.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. VACCINES

Provided herein is a vaccine comprising an antigen and an adjuvant. The vaccine can increase antigen presentation and the overall immune response to the antigen in an individual. The combination of antigen and adjuvant induces the immune system more efficiently than a vaccine comprising the antigen alone. The vaccine can further modify epitope presentation within the antigen to induce a greater immune response to the antigen than a vaccine comprising the antigen alone. The vaccine can further induce an immune response when administered to different tissues such as the muscle and the skin.

The vaccine of the present invention can have features required of effective vaccines such as being safe so that the vaccine itself does not cause illness or death; being protective against illness resulting from exposure to live pathogens such as viruses or bacteria; inducing neutralizing antibody to prevent infection of cells; inducing protective T cell responses against intracellular pathogens; and providing ease of administration, few side effects, biological stability, and low cost per dose. The vaccine can accomplish some or all of these features by combining the antigen with the adjuvant as discussed below.

a. Adjuvant

The vaccine can comprise an adjuvant and antigen as discussed below. The adjuvant can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the adjuvant by a peptide bond. The amino acid sequence can be a protein, a peptide, a variant thereof, a fragment thereof, or a combination thereof.

(1) IL-23

The adjuvant can be interleukin-23 (IL-23). IL-23 can be a heterodimer of the p19 and p40 subunits, fragments thereof, variants thereof, or the combination thereof. The p40 subunit can also be used by interleukin-12 (IL-12), while the p19 subunit can be distinct to IL-23. IL-23 is secreted by activated dendritic cells and activated macrophages in peripheral tissues (e.g., skin, intestinal mucosa, lung, etc.), and controls inflammation in peripheral tissues. Overexpression of the p19 subunit can produce inflammation in multiple organs and epithelial tissues, for example, the skin. When IL-23 function is disrupted by knockout of the p19 or p40 subunit, the symptoms of inflammatory diseases such as psoriasis, multiple sclerosis, and inflammatory bowel disease are less severe. The knockouts, however, result in decreased resistance to pathogens and reduced interferon-gamma (IFN-γ) production. IFN-γ has antiviral, immunoregulatory, and anti-tumor properties and can alter transcription in up to 30 genes, producing a variety of physiological and cellular responses. These effects include promoting natural killer (NK) cell activity, causing normal cells to increase expression of class I MHC molecules, increasing antigen presentation and lysosome activity in macrophages, inducing nitric oxide synthase (iNOS), and promoting Th1 differentiation in cellular immunity with regards to cytotoxic CD8$^+$ T cells while suppressing Th2 differentiation in humoral (antibody) response.

IL-23, similar to IL-12, can stimulate IFN-γ production. IL-12 can activate naïve T cells to induce IFN-γ production while IL-23 can act on memory T cells to induce IFN-γ production. Inclusion of IL-23 in the vaccine can induce IFN-γ production by at least about 1.5-fold, at least about 2-fold, at least about 3-fold, at least about 4-fold, at least about 5-fold, at least about 8-fold, and at least about 10-fold as compared to a vaccine not including IL-23. Inclusion of IL-23 in the vaccine can induce IFN-γ production by at least about 2-fold as compared to a vaccine not including IL-23. Inclusion of IL-23 in the vaccine can induce IFN-γ production by at least about 3-fold as compared to a vaccine not including IL-23.

In other instances, plasmacytoid and myeloid dendritic cells can produce and/or respond to both IL-12 and IL-23. Skin dendritic cells (e.g., Langerhans cells and dermal dendritic cells), however, can only produce and/or respond to IL-23, suggesting that IL-12 and IL-23 can have different activity profiles across tissues. IL-23 can have activity in muscle, skin, and other tissues unlike IL-12.

In other instances, IL-23 can promote the inflammatory response by amplifying and stabilizing T helper type 17 (Th17) cell populations, which were initially driven to differentiate by transforming growth factor-β (TGF-β), IL-1, and IL-6. Th17 cells can function at mucosal surfaces and trigger pro-inflammatory signals that promote neutrophil mobilization and the expression of antimicrobial factors. In addition to host defense, Th17 cells can be involved in the pathology of inflammatory diseases.

Th17 cells can trigger the pro-inflammatory signals by producing the cytokines IL-17 (i.e., IL-17A), IL-17F, and IL-22. IL-17 can mediate signaling through ACT1-dependent pathways, which lead to activation of pro-inflammatory factors such as NF-κB. NF-κB can be associated with innate immunity. IL-22 can promote JAK-STAT3 signaling, which is associated with adaptive immunity. Accordingly, Th17 cells, unlike Th1 and Th2 cells, can be considered a bridge between adaptive and innate immunity. As such, a vaccine including the adjuvant IL-23 can increase the immune response to the antigen by driving the inflammatory responses of both adaptive and innate immunity in multiple tissues through Th17 cells. Vaccines including cytokine adjuvants other than IL-23 such as IL-12, which promotes Th1 cells, and IL-4, which promotes Th2 cells, are unable to increase the immune response in such a fashion as IL-23 because Th1 cells and Th2 cells do not activate both adaptive and innate immunity. Accordingly, vaccines including the antigen and IL-23 are superior over other vaccines.

IL-23 can increase or boost the immune response to the antigen in a subject. The antigen is described in more detail below. In some instances, IL-23 can increase the immune response to the antigen by about 75% to about 200%. Alternatively, IL-23 can increase the immune response to the antigen by about 90% to about 130%. In still other alternative embodiments, IL-23 can increase the immune response to the antigen by about 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129% or 130%.

In other embodiments, IL-23 can increase or boost the immune response to the antigen by at least about 1.5-fold, at least about 2-fold, at least about 2.5-fold, at least about 3-fold, at least about 4-fold, at least about 5-fold, at least about 6-fold, at least about 7-fold, at least about 8-fold, at least about 9-fold, or at least about 10-fold when the herein described vaccines are administered to a subject in need thereof.

In some embodiments, IL-23 can modify or alter immune system recognition of at least one epitope in the antigen in any number of tissues in the individual, for example, a skin tissue and a muscle tissue. The antigen is described in more detail below. Such altered recognition of the at least one epitope can induce a greater immune response in a subject administered the herein described vaccines as compared to a subject administered a vaccine comprising a nucleic acid corresponding to the antigen alone.

IL-23 may also modify or change the presentation of one or more epitopes in the antigen, for example, by allowing a previously unrecognized epitope to be recognized by the immune system, thereby increasing the immune response in the subject to the antigen. The modified presentation, and thus the increased immune response, can occur in any number of tissues in the subject, for example, a skin tissue and a muscle tissue.

A nucleic acid encoding the p19 subunit of IL-23 can be from any number of organisms, for example, mouse (*Mus musculus*), macaque (*Macacac mulatta*), and human (*Homo* sapiens). The nucleic acid encoding the p19 subunit can be optimized with regards to codon usage and corresponding RNA transcripts. The nucleic acid encoding the p19 subunit can be codon and RNA optimized for expression. In some embodiments, the nucleic acid encoding the p19 subunit of IL-23 can include a Kozak sequence (e.g., GCC ACC) to increase the efficiency of translation. The nucleic acid encoding the p19 subunit of IL-23 can include multiple stop codons (e.g., TGA TGA) to increase the efficiency of translation termination. The nucleic acid encoding the p19 subunit of IL-23 can also include a nucleotide sequence encoding a IgE leader sequence. The IgE leader sequence can be located 5' to the p19 subunit in the nucleic acid. In some embodiments, the nucleic acid encoding the p19 subunit of IL-23 is free of or does not contain a nucleotide sequence encoding the IgE leader sequence.

The mouse p19 subunit can be the nucleic acid sequence SEQ ID NO: 1, which encodes for GenBank Accession No. EDL24554.1 (SEQ ID NO: 2). In some embodiments, the mouse p19 subunit can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:1. In other embodiments, the mouse p19 subunit can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2. The mouse p19 subunit can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2.

The mouse p19 subunit can be the optimized nucleic acid sequence shown in FIG. 2, which also encodes for GenBank Accession No. EDL24554.1 (SEQ ID NO:2). The mouse p19 subunit can be the optimized nucleic acid sequence SEQ ID NO:18, which encodes for SEQ ID NO:19. In some embodiments, the mouse p19 subunit can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:18. In other embodiments, the mouse p19 subunit can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:19. The mouse p19 subunit can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:19.

The mouse p19 subunit can be the optimized nucleic acid sequence located at 2549 to 3199 of plasmid WLV009-mIL-23 Opt (SEQ ID NO:13), which encodes for SEQ ID NO:19. In some embodiments, the mouse p19 subunit can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in 2549 to 3199 of plasmid WLV009-mIL-23 Opt (SEQ ID NO:13).

The macaque p19 subunit can be the nucleic acid sequence SEQ ID NO: 3, which encodes for GenBank Accession No. NP_001181598.1 (SEQ ID NO: 4). In some embodiments, the macaque p19 subunit can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:3. In other embodiments, the macaque p19 subunit can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:4. The macaque p19 subunit can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:4.

The human p19 subunit can be the nucleic acid sequence SEQ ID NO:5, which encodes for GenBank Accession No. AAH67511.1 (SEQ ID NO:6). In some embodiments, the human p19 subunit can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:5. In other embodiments, the human p19 subunit can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:6. The human p19 subunit can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:6.

The human p19 subunit can be the optimized nucleic acid sequence SEQ ID NO:22. In some embodiments, the human p19 subunit can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:22.

A nucleic acid encoding the p40 subunit of IL-23 can be from any number of organisms, for example, mouse (*Mus musculus*), macaque (*Macacac mulatta*), and human (*Homo sapiens*). The nucleic acid encoding the p40 subunit can be optimized with regards to codon usage and corresponding RNA transcripts. The nucleic acid encoding the p40 subunit can be codon and RNA optimized for expression. In some embodiments, the nucleic acid encoding the p40 subunit of IL-23 can include a Kozak sequence (e.g., GCC ACC) to increase the efficiency of translation. The nucleic acid encoding the p40 subunit of IL-23 can include multiple stop codons (e.g., TGA TGA) to increase the efficiency of translation termination. The nucleic acid encoding the p40 subunit can also encode an immunoglobulin E (IgE) leader sequence. The IgE leader sequence can be located 5' to the p40 subunit in the nucleic acid. The nucleic acid encoding the p40 subunit of IL-23 can also include a nucleotide sequence encoding the IgE leader sequence. In some embodiments, the nucleic acid encoding the p40 subunit of IL-23 is free of or does not contain a nucleotide sequence encoding the IgE leader sequence.

The mouse p40 subunit can be the nucleic acid sequence SEQ ID NO: 7, which encodes for GenBank Accession No. NP_032378.1 (SEQ ID NO: 8). In some embodiments, the mouse p40 subunit can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:7. In other embodiments, the mouse p40 subunit can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:8. The mouse p40 subunit can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:8.

Figure 2:
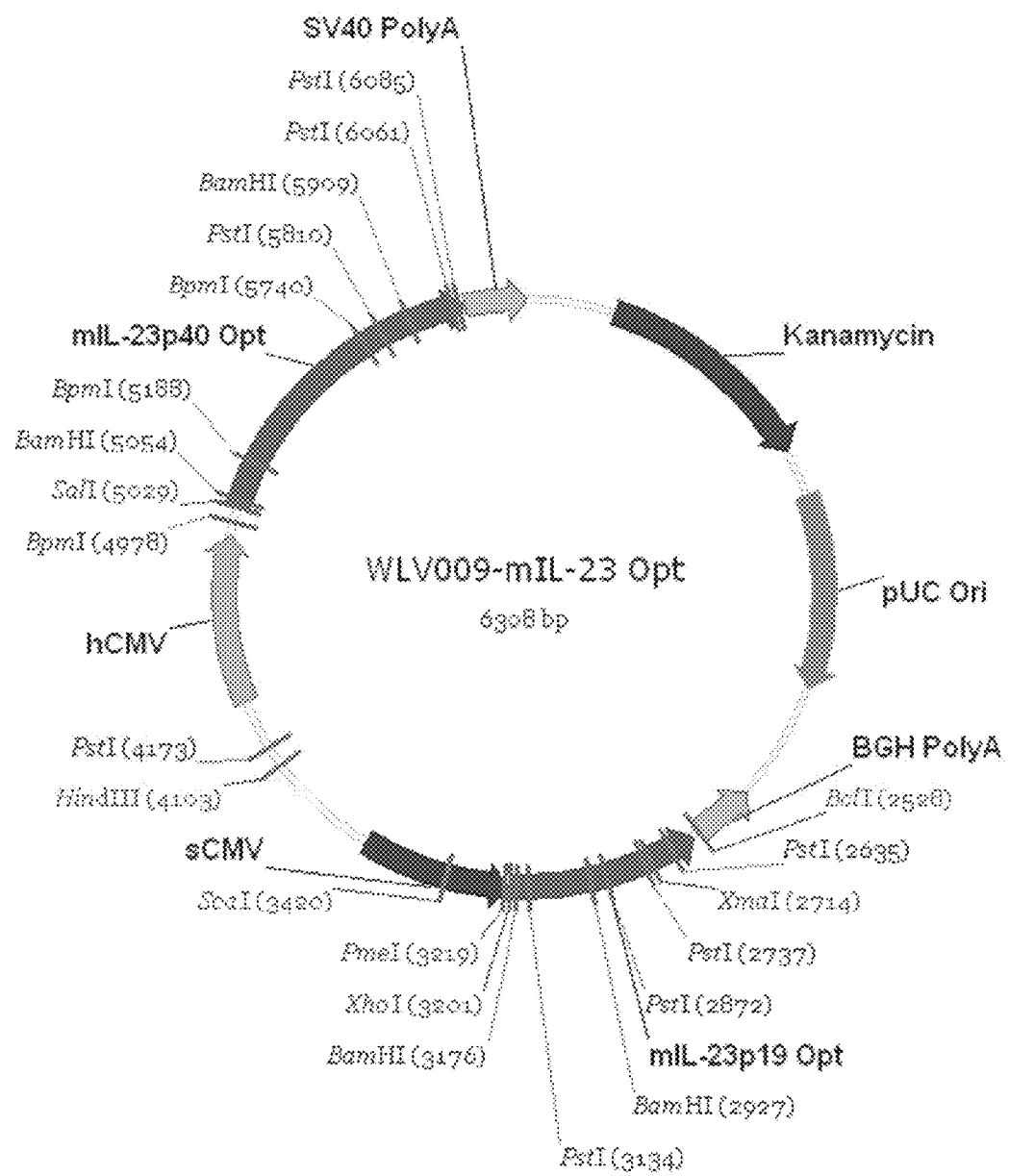
FIG. 2 shows a map of the plasmid WLV009-mIL-23 Opt (SEQ ID NO:13), which includes optimized nucleic acids encoding for the mouse p19 and p40 subunits of IL-23. Note that in the plasmid WLV009-mIL-23 Opt (SEQ ID NO:13), the optimized nucleic acids encoding for the mouse p19 and p40 subunits of IL-23 are in opposite orientations relative to one another. Therefore, the nucleic acid sequence presented in SEQ ID NO:13 is the anti-sense or anti-parallel strand relative to the optimized nucleic acid sequence encoding mouse p19 (SEQ ID NO:18), but is the sense strand relative to the optimized nucleic acid sequence encoding mouse p40 (SEQ ID NO:20).

The mouse p40 subunit can be the optimized nucleic acid sequence shown in FIG. 2, which also encodes for GenBank Accession No. NP_032378.1 (SEQ ID NO:8). The mouse p40 subunit can be the optimized nucleic acid sequence SEQ ID NO:20, which encodes for SEQ ID NO:21. In some embodiments, the mouse p40 subunit can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:20. In other embodiments, the mouse p40 subunit can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:21. The mouse p40 subunit can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:21.

The mouse p40 subunit can be the optimized nucleic acid sequence located at 5034 to 6101 of plasmid WLV009-mIL-23 Opt (SEQ ID NO:13), which encodes for SEQ ID NO:21. In some embodiments, the mouse p40 subunit can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in 5034 to 6101 of plasmid WLV009-mIL-23 Opt (SEQ ID NO:13).

The macaque p40 subunit can be the nucleic acid sequence SEQ ID NO: 9, which encodes for GenBank Accession No. NP_001038190. (SEQ ID NO: 10). In some embodiments, the macaque p40 subunit can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:9. In other embodiments, the macaque p40 subunit can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:10. The macaque p40 subunit can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:10.

The human p40 subunit can be the nucleic acid sequence SEQ ID NO: 11, which encodes for GenBank Accession No. AAG32620.1 (SEQ ID NO: 12). In some embodiments, the human p40 subunit can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:11. In other embodiments, the human p40 subunit can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:12. The human p40 subunit can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:12.

The human p40 subunit can be the optimized nucleic acid sequence SEQ ID NO:23. In some embodiments, the human p40 subunit can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:23.

Some embodiments relate to fragments of SEQ ID NO:1, SEQ ID NO:3, SEQ ID NO:5, SEQ ID NO:7, SEQ ID NO:9, SEQ ID NO:11, SEQ ID NO:18, SEQ ID NO:20, SEQ ID NO:22, SEQ ID NO:23, 2549 to 3199 of SEQ ID NO:13, and 5034 to 6101 of SEQ ID NO:13 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:1, SEQ ID NO:3, SEQ ID NO:5, SEQ ID NO:7, SEQ ID NO:9, SEQ ID NO:11, SEQ ID NO:18, SEQ ID NO:20, SEQ ID NO:22, SEQ ID NO:23, 2549 to 3199 of SEQ ID NO:13, and/or 5034 to 6101 of SEQ ID NO:13. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of SEQ ID NO:1, SEQ ID NO:3, SEQ ID NO:5, SEQ ID NO:7, SEQ ID NO:9, SEQ ID NO:11, SEQ ID NO:18, SEQ ID NO:20, SEQ ID NO:22, SEQ ID NO:23, 2549 to 3199 of SEQ ID NO:13, and 5034 to 6101 of SEQ ID NO:13 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:1, SEQ ID NO:3, SEQ ID NO:5, SEQ ID NO:7, SEQ ID NO:9, SEQ ID NO:11, SEQ ID NO:18, SEQ ID NO:20, SEQ ID NO:22, SEQ ID NO:23, 2549 to 3199 of SEQ ID NO:13, and/or 5034 to 6101 of SEQ ID NO:13. Some embodiments relate to fragments that have 96% or greater identity to the fragments of IL-23 (i.e., p19 subunit and/or p40 subunit) nucleic acid sequences herein. Some embodiments relate to fragments that have 97% or greater identity to the fragments of IL-23 (i.e., p19 subunit and/or p40 subunit) nucleic acid sequences herein. Some embodiments relate to fragments that have 98% or greater identity to the fragments of IL-23 (i.e., p19 subunit and/or p40 subunit) nucleic acid sequences herein. Some embodiments relate to fragments that have 99% or greater identity to the fragments of IL-23 (i.e., p19 subunit and/or p40 subunit) nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NO:2, SEQ ID NO:4, SEQ ID NO:6, SEQ ID NO:8, SEQ ID NO:10, SEQ ID NO:12, SEQ ID NO:19, and SEQ ID NO:21 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:2, SEQ ID NO:4, SEQ ID NO:6, SEQ ID NO:8, SEQ ID NO:10, SEQ ID NO:12, SEQ ID NO:19, and/or SEQ ID NO:21. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NO:2, SEQ ID NO:4, SEQ ID NO:6, SEQ ID NO:8, SEQ ID NO:10, SEQ ID NO:12, SEQ ID NO:19, and SEQ ID NO:21 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:2, SEQ ID NO:4, SEQ ID NO:6, SEQ ID NO:8, SEQ ID NO:10, SEQ ID NO:12, SEQ ID NO:19, and/or SEQ ID NO:21. Some embodiments relate to fragments having 96% or greater identity to the fragments of IL-23 (i.e., p19 subunit and/or p40 subunit) protein sequences herein. Some embodiments relate to fragments having 97% or greater identity to the fragments of IL-23 (i.e., p19 subunit and/or p40 subunit) protein sequences herein. Some embodiments relate to fragments having 98% or greater identity to the fragments of IL-23 (i.e., p19 subunit and/or p40 subunit) protein sequences herein. Some embodiments relate to fragments having 99% or greater identity to the fragments of IL-23 (i.e., p19 subunit and/or p40 subunit) protein sequences herein. In some embodiments, fragments include a leader sequence, for example, an immunoglobulin leader sequence such as the IgE leader sequence. In some embodiments, the fragments are free of a leader sequence.

b. Antigen

The vaccine can comprise an antigen or fragment or variant thereof and an adjuvant as discussed above. The antigen can be anything that induces an immune response in a subject. Purified antigens are not usually strongly immunogenic on their own and are therefore combined with the adjuvant as described above. The immune response induced by the antigen can be boosted or increased when combined with the adjuvant. Such an immune response can be a humoral immune response and/or a cellular immune response. In some embodiments, the combination of the adjuvant and the antigen can boost or increase a cellular immune response in the subject. In other embodiments, the combination of the adjuvant and the antigen can boost or increase a humoral immune response in the subject.

The antigen can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the antigen by a peptide bond. The amino acid sequence can be a protein, a peptide, a variant thereof, a fragment thereof, or a combination thereof.

The antigen can be contained in a protein, a nucleic acid, or a fragment thereof, or a variant thereof, or a combination thereof from any number of organisms, for example, a virus, a parasite, a bacterium, a fungus, or a mammal. The antigen can be associated with an autoimmune disease, allergy, or asthma. In other embodiments, the antigen can be associated with cancer, herpes, influenza, hepatitis B, hepatitis C, human papilloma virus (HPV), or human immunodeficiency virus (HIV). As discussed below, the antigen of the vaccine can be selected from a group consisting of a human papilloma virus (HPV) antigen, an HIV antigen, an influenza antigen, a *Plasmodium falciparum* antigen and a fragment thereof. The HPV antigen can be selected from the group consisting of HPV16 E6 antigen, an HPV16 E7 antigen and a combination thereof. The HIV antigen can be selected from the group consisting of Env A, Env B, Env C, Env D, B Nef-Rev, Gag, and any combination thereof. The influenza antigen can be selected from the group consisting of H1 HA, H2 HA, H3 HA, H5 HA, BHA antigen and any combination thereof. The *Plasmodium falciparum* antigen may include a circumsporozoite (CS) antigen.

Some antigens can induce a strong immune response. Other antigens can induce a weak immune response. The antigen can elicit a greater immune response when combined with the adjuvant as described above.

(1) Viral Antigens

The antigen can be a viral antigen, or fragment thereof, or variant thereof. The viral antigen can be from a virus from one of the following families: Adenoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. The viral antigen can be from papilloma viruses, for example, human papillomoa virus (HPV), human immunodeficiency virus (HIV), polio virus, hepatitis B virus, hepatitis C virus, smallpox virus (Variola major and minor), vaccinia virus, influenza virus, rhinoviruses, dengue fever virus, equine encephalitis viruses, rubella virus, yellow fever virus, Norwalk virus, hepatitis A virus, human T-cell leukemia virus (HTLV-I), hairy cell leukemia virus (HTLV-II), California encephalitis virus, Hanta virus (hemorrhagic fever), rabies virus, Ebola fever virus, Marburg virus, measles virus, mumps virus, respiratory syncytial virus (RSV), herpes simplex 1 (oral herpes), herpes simplex 2 (genital herpes), herpes zoster (varicella-zoster, a.k.a., chickenpox), cytomegalovirus (CMV), for example human CMV, Epstein-Barr virus (EBV), flavivirus, foot and mouth disease virus, chikungunya virus, lassa virus, arenavirus, or cancer causing virus.

(a) Hepatitis Antigen

IL-23 can be associated or combined with a hepatitis virus antigen (i.e., hepatitis antigen), or fragment thereof, or variant thereof. The hepatitis antigen can be an antigen or immunogen from hepatitis A virus (HAV), hepatitis B virus (HBV), hepatitis C virus (HCV), hepatitis D virus (HDV), and/or hepatitis E virus (HEV). In some embodiments, the hepatitis antigen can be a heterologous nucleic acid molecule(s), such as a plasmid(s), which encodes one or more of the antigens from HAV, HBV, HCV, HDV, and HEV. The hepatitis antigen can be full-length or immunogenic fragments of full-length proteins.

The hepatitis antigen can comprise consensus sequences and/or one or more modifications for improved expression. Genetic modifications, including codon optimization, RNA optimization, and the addition of a highly efficient immunoglobulin leader sequence to increase the immunogenicity of the constructs, can be included in the modified consensus sequences. The consensus hepatitis antigen may comprise a signal peptide such as an immunoglobulin signal peptide such as an IgE or IgG signal peptide, and in some embodiments, may comprise an HA tag. The immunogens can be designed to elicit stronger and broader cellular immune responses than corresponding codon optimized immunogens.

The hepatitis antigen can be an antigen from HAV. The hepatitis antigen can be a HAV capsid protein, a HAV non-structural protein, a fragment thereof, a variant thereof, or a combination thereof.

The hepatitis antigen can be an antigen from HCV. The hepatitis antigen can be a HCV nucleocapsid protein (i.e., core protein), a HCV envelope protein (e.g., E1 and E2), a HCV non-structural protein (e.g., NS1, NS2, NS3, NS4a, NS4b, NS5a, and NS5b), a fragment thereof, a variant thereof, or a combination thereof.

The hepatitis antigen can be an antigen from HDV. The hepatitis antigen can be a HDV delta antigen, fragment thereof, or variant thereof.

The hepatitis antigen can be an antigen from HEV. The hepatitis antigen can be a HEV capsid protein, fragment thereof, or variant thereof.

The hepatitis antigen can be an antigen from HBV. The hepatitis antigen can be a HBV core protein, a HBV surface protein, a HBV DNA polymerase, a HBV protein encoded by gene X, fragment thereof, variant thereof, or combination thereof. The hepatitis antigen can be a HBV genotype A core protein, a HBV genotype B core protein, a HBV genotype C core protein, a HBV genotype D core protein, a HBV genotype E core protein, a HBV genotype F core protein, a HBV genotype G core protein, a HBV genotype H core protein, a HBV genotype A surface protein, a HBV genotype B surface protein, a HBV genotype C surface protein, a HBV genotype D surface protein, a HBV genotype E surface protein, a HBV genotype F surface protein, a HBV genotype G surface protein, a HBV genotype H surface protein, fragment thereof, variant thereof, or combination thereof. The hepatitis antigen can be a consensus HBV core protein, or a consensus HBV surface protein.

In some embodiments, the hepatitis antigen can be a HBV genotype A consensus core DNA sequence construct, an IgE leader sequence linked to a consensus sequence for HBV genotype A core protein, or a HBV genotype A consensus core protein sequence.

In other embodiments, the hepatitis antigen can be a HBV genotype B consensus core DNA sequence construct, an IgE leader sequence linked to a consensus sequence for HBV genotype B core protein, or a HBV genotype B consensus core protein sequence.

In still other embodiments, the hepatitis antigen can be a HBV genotype C consensus core DNA sequence construct, an IgE leader sequence linked to a consensus sequence for HBV genotype C core protein, or a HBV genotype C consensus core protein sequence.

In some embodiments, the hepatitis antigen can be a HBV genotype D consensus core DNA sequence construct, an IgE leader sequence linked to a consensus sequence for HBV genotype D core protein, or a HBV genotype D consensus core protein sequence.

In other embodiments, the hepatitis antigen can be a HBV genotype E consensus core DNA sequence construct, an IgE leader sequence linked to a consensus sequence for HBV genotype E core protein, or a HBV genotype E consensus core protein sequence.

In some embodiments, the hepatitis antigen can be a HBV genotype F consensus core DNA sequence construct, an IgE leader sequence linked to a consensus sequence for HBV genotype F core protein, or a HBV genotype F consensus core protein sequence.

In other embodiments, the hepatitis antigen can be a HBV genotype G consensus core DNA sequence construct, an IgE leader sequence linked to a consensus sequence for HBV genotype G core protein, or a HBV genotype G consensus core protein sequence.

In some embodiments, the hepatitis antigen can be a HBV genotype H consensus core DNA sequence construct, an IgE leader sequence linked to a consensus sequence for HBV genotype H core protein, or a HBV genotype H consensus core protein sequence.

In still other embodiments, the hepatitis antigen can be a HBV genotype A consensus surface DNA sequence construct, an IgE leader sequence linked to a consensus sequence for HBV genotype A surface protein, or a HBV genotype A consensus surface protein sequence.

In some embodiments, the hepatitis antigen can be a HBV genotype B consensus surface DNA sequence construct, an IgE leader sequence linked to a consensus sequence for HBV genotype B surface protein, or a HBV genotype B consensus surface protein sequence.

In other embodiments, the hepatitis antigen can be a HBV genotype C consensus surface DNA sequence construct, an IgE leader sequence linked to a consensus sequence for HBV genotype C surface protein, or a HBV genotype C consensus surface protein sequence.

In still other embodiments, the hepatitis antigen can be a HBV genotype D consensus surface DNA sequence construct, an IgE leader sequence linked to a consensus sequence for HBV genotype D surface protein, or a HBV genotype D consensus surface protein sequence.

In some embodiments, the hepatitis antigen can be a HBV genotype E consensus surface DNA sequence construct, an IgE leader sequence linked to a consensus sequence for HBV genotype E surface protein, or a HBV genotype E consensus surface protein sequence.

In other embodiments, the hepatitis antigen can be a HBV genotype F consensus surface DNA sequence construct, an IgE leader sequence linked to a consensus sequence for HBV genotype F surface protein, or a HBV genotype F consensus surface protein sequence.

In still other embodiments, the hepatitis antigen can be a HBV genotype G consensus surface DNA sequence construct, an IgE leader sequence linked to a consensus sequence for HBV genotype G surface protein, or a HBV genotype G consensus surface protein sequence.

In other embodiments, the hepatitis antigen can be a HBV genotype H consensus surface DNA sequence construct, an IgE leader sequence linked to a consensus sequence for HBV genotype H surface protein, or a HBV genotype H consensus surface protein sequence.

(b) Human Papilloma Virus (HPV) Antigen

IL-23 can be associated or combined with a human papilloma virus (HPV) antigen, or fragment thereof, or variant thereof. The HPV antigen can be from HPV types 16, 18, 31, 33, 35, 45, 52, and 58, which cause cervical cancer, rectal cancer, and/or other cancers. The HPV antigen can be from HPV types 6 and 11, which cause genital warts, and are known to be causes of head and neck cancer.

The HPV antigens can be the HPV E6 or E7 domains from each HPV type. For example, for HPV type 16 (HPV16), the HPV16 antigen can include the HPV16 E6 antigen, the HPV16 E7 antigen, fragments, variants, or combinations thereof. Similarly, the HPV antigen can be HPV 6 E6 and/or E7, HPV 11 E6 and/or E7, HPV 18 E6 and/or E7, HPV 31 E6 and/or E7, HPV 33 E6 and/or E7, HPV 52 E6 and/or E7, or HPV 58 E6 and/or E7, fragments, variants, or combinations thereof.

(c) RSV Antigen

IL-23 can also be associated or combined with an RSV antigen or fragment thereof, or variant thereof. The RSV antigen can be a human RSV fusion protein (also referred to herein as "RSV F", "RSV F protein" and "F protein"), or fragment or variant thereof. The human RSV fusion protein can be conserved between RSV subtypes A and B. The RSV antigen can be a RSV F protein, or fragment or variant thereof, from the RSV Long strain (GenBank AAX23994.1). The RSV antigen can be a RSV F protein from the RSV A2 strain (GenBank AAB59858.1), or a fragment or variant thereof. The RSV antigen can be a monomer, a dimer or trimer of the RSV F protein, or a fragment or variant thereof. The RSV antigen can be consensus RSV F amino acid sequence, or fragment or variant thereof. The RSV antigen can be an optimized nucleic acid encoding RSV F amino acid sequence or fragment or variant thereof.

The postfusion form of RSV F elicits high titer neutralizing antibodies in immunized animals and protects the animals from RSV challenge. The present invention utilizes this immunoresponse in the claimed vaccines. According to the invention, the RSV F protein can be in a prefusion form or a postfusion form.

The RSV antigen can also be human RSV attachment glycoprotein (also referred to herein as "RSV G", "RSV G protein" and "G protein"), or fragment or variant thereof. The human RSV G protein differs between RSV subtypes A and B. The antigen can be RSV G protein, or fragment or variant thereof, from the RSV Long strain (GenBank AAX23993). The RSV antigen can be RSV G protein from: the RSV subtype B isolate H5601, the RSV subtype B isolate H1068, the RSV subtype B isolate H5598, the RSV subtype B isolate H1123, or a fragment or variant thereof. The RSV antigen can be a consensus RSV G amino acid sequence, or fragment or variant thereof. The RSV antigen can be an optimized nucleic acid encoding RSV G amino acid sequence or fragment or variant thereof.

In other embodiments, the RSV antigen can be human RSV non-structural protein 1 ("NS1 protein"), or fragment or variant thereof. For example, the RSV antigen can be RSV NS1 protein, or fragment or variant thereof, from the RSV Long strain (GenBank AAX23987.1). The RSV antigen human can also be RSV non-structural protein 2 ("NS2 protein"), or fragment or variant thereof. For example, the RSV antigen can be RSV NS2 protein, or fragment or variant thereof, from the RSV Long strain (GenBank AAX23988.1). The RSV antigen can further be human RSV nucleocapsid ("N") protein, or fragment or variant thereof. For example, the RSV antigen can be RSV N protein, or fragment or variant thereof, from the RSV Long strain (GenBank AAX23989.1). The RSV antigen can be human RSV Phosphoprotein ("P") protein, or fragment or variant thereof. For example, the RSV antigen can be RSV P protein, or fragment or variant thereof, from the RSV Long strain (GenBank AAX23990.1). The RSV antigen also can be human RSV Matrix protein ("M") protein, or fragment or variant thereof. For example, the RSV antigen can be RSV M protein, or fragment or variant thereof, from the RSV Long strain (GenBank AAX23991.1).

In still other embodiments, the RSV antigen can be human RSV small hydrophobic ("SH") protein, or fragment or variant thereof. For example, the RSV antigen can be RSV SH protein, or fragment or variant thereof, from the RSV Long strain (GenBank AAX23992.1). The RSV antigen can also be human RSV Matrix protein 2-1 ("M2-1") protein, or fragment or variant thereof. For example, the RSV antigen can be RSV M2-1 protein, or fragment or variant thereof, from the RSV Long strain (GenBank AAX23995.1). The RSV antigen can further be human RSV Matrix protein 2-2 ("M2-2") protein, or fragment or variant thereof. For example, the RSV antigen can be RSV M2-2 protein, or fragment or variant thereof, from the RSV Long strain (GenBank AAX23997.1). The RSV antigen human can be RSV Polymerase L ("L") protein, or fragment or variant thereof. For example, the RSV antigen can be RSV L protein, or fragment or variant thereof, from the RSV Long strain (GenBank AAX23996.1).

In further embodiments, the RSV antigen can have a consensus amino acid sequence of NS1, NS2, N, P, M, SH, M2-1, M2-2, or L protein. The RSV antigen can be a human RSV protein or recombinant antigen, such as any one of the proteins encoded by the human RSV genome.

In other embodiments, the RSV antigen can be, but is not limited to, the RSV F protein from the RSV Long strain, the RSV G protein from the RSV Long strain, the consensus RSV G amino acid sequence, the optimized nucleic acid encoding RSV G amino acid sequence, the human RSV genome of the RSV Long strain, the consensus RSV F amino acid sequence, the optimized nucleic acid encoding RSV F amino acid sequence, the RSV NS1 protein from the RSV Long strain, the RSV NS2 protein from the RSV Long strain, the RSV N protein from the RSV Long strain, the RSV P protein from the RSV Long strain, the RSV M protein from the RSV Long strain, the RSV SH protein from the RSV Long strain, the RSV M2-1 protein from the RSV Long strain, for the RSV M2-2 protein from the RSV Long strain, the RSV L protein from the RSV Long strain, the RSV G protein from the RSV subtype B isolate H5601, the RSV G protein from the RSV subtype B isolate H1068, for the RSV G protein from the RSV subtype B isolate H5598, the RSV G protein from the RSV subtype B isolate H1123, or fragment thereof, or variant thereof.

(d) Influenza Antigen

IL-23 can be associated or combined with an influenza antigen or fragment thereof, or variant thereof. The influenza antigens are those capable of eliciting an immune response in a mammal against one or more influenza serotypes. The antigen can comprise the full length translation product HA0, subunit HA1, subunit HA2, a variant thereof, a fragment thereof or a combination thereof. The influenza hemagglutinin antigen can be a consensus sequence derived from multiple strains of influenza A serotype H1, a consensus sequence derived from multiple strains of influenza A serotype H2, a hybrid sequence containing portions of two different consensus sequences derived from different sets of multiple strains of influenza A serotype H1 or a consensus sequence derived from multiple strains of influenza B. The influenza hemagglutinin antigen can be from influenza B.

The influenza antigen can also contain at least one antigenic epitope that can be effective against particular influenza immunogens against which an immune response can be induced. The antigen may provide an entire repertoire of immunogenic sites and epitopes present in an intact influenza virus. The antigen may be a consensus hemagglutinin antigen sequence that can be derived from hemagglutinin antigen sequences from a plurality of influenza A virus strains of one serotype such as a plurality of influenza A virus strains of serotype H1 or of serotype H2. The antigen may be a hybrid consensus hemagglutinin antigen sequence that can be derived from combining two different consensus hemagglutinin antigen sequences or portions thereof. Each of two different consensus hemagglutinin antigen sequences may be derived from a different set of a plurality of influenza A virus strains of one serotype such as a plurality of influenza A virus strains of serotype H1. The antigen may be a consensus hemagglutinin antigen sequence that can be derived from hemagglutinin antigen sequences from a plurality of influenza B virus strains.

In some embodiments, the influenza antigen can be H1 HA, H2 HA, H3 HA, H5 HA, or a BHA antigen. Alternatively, the influenza antigen can be a consensus hemagglutinin antigen comprising a consensus H1 amino acid sequence or a consensus H2 amino acid sequence. The consensus hemagglutinin antigen may be a synthetic hybrid consensus H1 sequence comprising portions of two different consensus H1 sequences, which are each derived from a different set of sequences from the other. An example of a consensus HA antigen that is a synthetic hybrid consensus H1 protein is a protein comprising the U2 amino acid sequence. The consensus hemagglutinin antigen may be a consensus hemagglutinin protein derived from hemagglutinin sequences from influenza B strains, such as a protein comprising the consensus BHA amino acid sequence.

The consensus hemagglutinin antigen may further comprise one or more additional amino acid sequence elements. The consensus hemagglutinin antigen may further comprise on its N-terminus, an IgE or IgG leader amino acid sequence. The consensus hemagglutinin antigen may further comprise an immunogenic tag, which is a unique immunogenic epitope that can be detected by readily available antibodies. An example of such an immunogenic tag is the 9 amino acid influenza HA Tag, which may be linked on the consensus hemagglutinin C-terminus. In some embodiments, consensus hemagglutinin antigen may further comprise on its N-terminus, an IgE or IgG leader amino acid sequence and on its C-terminus, an HA tag.

The consensus hemagglutinin antigen may be a consensus hemagglutinin protein that consists of consensus influenza amino acid sequences or fragments and variants thereof. The consensus hemagglutinin antigen may be a consensus hemagglutinin protein that comprises non-influenza protein sequences and influenza protein sequences or fragments and variants thereof.

Examples of a consensus H1 protein include those that may consist of the consensus H1 amino acid sequence or those that further comprise additional elements such as an IgE leader sequence, or an HA Tag or both an IgE leader sequence and an HA Tag.

Examples of consensus H2 proteins include those that may consist of the consensus H2 amino acid sequence or those that further comprise an IgE leader sequence, or an HA Tag, or both an IgE leader sequence and an HA Tag.

Examples of hybrid consensus H1 proteins include those that may consist of the consensus U2 amino acid sequence or those that further comprise an IgE leader sequence, or an HA Tag, or both an IgE leader sequence and an HA Tag.

Examples of hybrid consensus influenza B hemagglutinin proteins include those that may consist of the consensus BHA amino acid sequence or it may comprise an IgE leader sequence, or a an HA Tag, or both an IgE leader sequence and an HA Tag.

The consensus hemagglutinin protein can be encoded by a consensus hemagglutinin nucleic acid, a variant thereof or a fragment thereof. Unlike the consensus hemagglutinin protein which may be a consensus sequence derived from a plurality of different hemagglutinin sequences from different strains and variants, the consensus hemagglutinin nucleic acid refers to a nucleic acid sequence that encodes a consensus protein sequence and the coding sequences used may differ from those used to encode the particular amino acid sequences in the plurality of different hemagglutinin sequences from which the consensus hemagglutinin protein sequence is derived. The consensus nucleic acid sequence may be codon optimized and/or RNA optimized. The consensus hemagglutinin nucleic acid sequence may comprise a Kozak sequence in the 5' untranslated region. The consensus hemagglutinin nucleic acid sequence may comprise nucleic acid sequences that encode a leader sequence. The coding sequence of an N terminal leader sequence is 5' of the hemagglutinin coding sequence. The N-terminal leader can facilitate secretion. The N-terminal leader can be an IgE leader or an IgG leader. The consensus hemagglutinin nucleic acid sequence can comprise nucleic acid sequences that encode an immunogenic tag. The immunogenic tag can be on the C-terminus of the protein and the sequence encoding it is 3' of the consensus HA coding sequence. The immunogenic tag provides a unique epitope for which there are readily available antibodies so that such antibodies can be used in assays to detect and confirm expression of the protein. The immunogenic tag can be an HA Tag at the C-terminus of the protein.

(e) Human Immunodeficiency Virus (HIV) Antigen

IL-23 can be associated or combined with an HIV antigen or fragment thereof, or variant thereof. HIV antigens can include modified consensus sequences for immunogens. Genetic modifications, including codon optimization, RNA optimization, and the addition of a highly efficient immunoglobin leader sequence to increase the immunogenicity of constructs, can be included in the modified consensus sequences. The novel immunogens can be designed to elicit stronger and broader cellular immune responses than a corresponding codon optimized immunogen.

In some embodiments, the HIV antigen can be a subtype A consensus envelope DNA sequence construct, an IgE leader sequence linked to a consensus sequence for Subtype A envelope protein, or a subtype A consensus Envelope protein sequence.

In other embodiments, the HIV antigen can be a subtype B consensus envelope DNA sequence construct, an IgE leader sequence linked to a consensus sequence for Subtype B envelope protein, or an subtype B consensus Envelope protein sequence In still other embodiments, the HIV antigen can be a subtype C consensus envelope DNA sequence construct, an IgE leader sequence linked to a consensus sequence for subtype C envelope protein, or a subtype C consensus envelope protein sequence.

In further embodiments, the HIV antigen can be a subtype D consensus envelope DNA sequence construct, an IgE leader sequence linked to a consensus sequence for Subtype D envelope protein, or a subtype D consensus envelope protein sequence.

In some embodiments, the HIV antigen can be a subtype B Nef-Rev consensus envelope DNA sequence construct, an IgE leader sequence linked to a consensus sequence for Subtype B Nef-Rev protein, or a Subtype B Nef-Rev consensus protein sequence In other embodiments, the HIV antigen can be a Gag consensus DNA sequence of subtype A, B, C and D DNA sequence construct, an IgE leader sequence linked to a consensus sequence for Gag consensus subtype A, B, C and D protein, or a consensus Gag subtype A, B, C and D protein sequence.

In still other embodiments the HIV antigen can be a MPol DNA sequence or a MPol protein sequence. The HIV antigen can be nucleic acid or amino acid sequences of Env A, Env B, Env C, Env D, B Nef-Rev, Gag, or any combination thereof.

(2) Parasite Antigens

The antigen can be a parasite antigen or fragment or variant thereof. The parasite can be a protozoa, helminth, or ectoparasite. The helminth (i.e., worm) can be a flatworm (e.g., flukes and tapeworms), a thorny-headed worm, or a round worm (e.g., pinworms). The ectoparasite can be lice, fleas, ticks, and mites.

The parasite can be any parasite causing the following diseases: Acanthamoeba keratitis, Amoebiasis, Ascariasis, Babesiosis, Balantidiasis, Baylisascariasis, Chagas disease, Clonorchiasis, *Cochliomyia*, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, and Trichuriasis.

The parasite can be Acanthamoeba, Anisakis, *Ascaris lumbricoides*, Botfly, *Balantidium coli*, Bedbug, *Cestoda* (tapeworm), Chiggers, *Cochliomyia hominivorax*, Entamoeba histolytica, *Fasciola hepatica, Giardia lamblia*, Hookworm, *Leishmania, Linguatula serrata*, Liver fluke, Loa loa, *Paragonimus*—lung fluke, Pinworm, *Plasmodium falciparum*, Schistosoma, *Strongyloides stercoralis*, Mite, Tapeworm, *Toxoplasma gondii, Trypanosoma*, Whipworm, or *Wuchereria bancrofti*.

(a) Malaria Antigen

IL-23 can be associated or combined with a malaria antigen (i.e., PF antigen or PF immunogen), or fragment thereof, or variant thereof. The antigen can be from a parasite causing malaria. The malaria causing parasite can be *Plasmodium falciparum*. The *Plasmodium falciparum* antigen can include the circumsporozoite (CS) antigen.

In some embodiments, the malaria antigen can be nucleic acid molecules such as plasmids which encode one or more of the *P. falciparum* immunogens CS; LSA1; TRAP; CelTOS; and Ama1. The immunogens may be full length or immunogenic fragments of full length proteins. The immunogens can comprise consensus sequences and/or modifications for improved expression.

In other embodiments, the malaria antigen can be a consensus sequence of TRAP, which is also referred to as SSP2, designed from a compilation of all full-length *Plasmodium falciparum* TRAP/SSP2 sequences in the GenBank database (28 sequences total). Consensus TRAP immunogens (i.e., ConTRAP immunogen) may comprise a signal peptide such as an immunoglobulin signal peptide such as an IgE or IgG signal peptide and in some embodiments, may comprise an HA Tag.

In still other embodiments, the malaria antigen can be CelTOS, which is also referred to as Ag2 and is a highly conserved *Plasmodium* antigen. Consensus CelTOS antigens (i.e., ConCelTOS immunogen) may comprise a signal peptide such as an immunoglobulin signal peptide such as an IgE or IgG signal peptide and in some embodiments, may comprise an HA Tag.

In further embodiments, the malaria antigen can be Ama1, which is a highly conserved *Plasmodium* antigen. The malaria antigen can also be a consensus sequence of Ama1 (i.e., ConAma1 immunogen) comprising in some instances, a signal peptide such as an immunoglobulin signal peptide such as an IgE or IgG signal peptide and in some embodiments, may comprise an HA Tag.

In some embodiments, the malaria antigen can be a consensus CS antigen (i.e., Consensus CS immunogen) comprising in some instances, a signal peptide such as an immunoglobulin signal peptide such as an IgE or IgG signal peptide and in some embodiments, may comprise an HA Tag.

In other embodiments, the malaria antigen can be a fusion protein comprising a combination of two or more of the PF proteins set forth herein. For example, fusion proteins may comprise two or more of Consensus CS immunogen, ConLSA1 immunogen, ConTRAP immunogen, ConCelTOS immunogen and ConAma1 immunogen linked directly adjacent to each other or linked with a spacer or one or more amino acids in between. In some embodiments, the fusion protein comprises two PF immunogens. In some embodiments the fusion protein comprises three PF immunogens. In some embodiments, the fusion protein comprises four PF immunogens. In some embodiments the fusion protein comprises five PF immunogens.

Fusion proteins with two Consensus PF immunogens may comprise: CS and LSA1; CS and TRAP; CS and CelTOS; CS and Ama1; LSA1 and TRAP; LSA1 and CelTOS; LSA1 and Ama1; TRAP and CelTOS; TRAP and Ama1; or CelTOS and Ama1. Fusion proteins with three Consensus PF immunogens may comprise: CS, LSA1 and TRAP; CS, LSA1 and CelTOS; CS, LSA1 and Ama1; LSA1, TRAP and CelTOS; LSA1, TRAP and Ama1; or TRAP, CelTOS and Ama1. Fusion proteins with four Consensus PF immunogens may comprise: CS, LSA1, TRAP and CelTOS; CS, LSA1, TRAP and Ama1; CS, LSA1, CelTOS and Ama1; CS, TRAP, CelTOS and Ama1; or LSA1, TRAP, CelTOS and Ama1. Fusion proteins with five Consensus PF immunogens may comprise CS or CS-alt, LSA1, TRAP, CelTOS and Ama1.

In some embodiments, the fusion proteins comprise a signal peptide linked to the N-terminus. In some embodiments, the fusion proteins comprise multiple signal peptides linked to the N-terminus of each Consensus PF immunogen. In some embodiments, a spacer may be included between PF immunogens of a fusion protein. In some embodiments, the spacer between PF immunogens of a fusion protein may be a proteolyic cleavage site. In some embodiments, the spacer may be a proteolyic cleavage site recognized by a protease found in cells to which the vaccine is intended to be administered and/or taken up. In some embodiments, a spacer may be included between PF immunogens of a fusion protein, wherein the spacer is a proteolyic cleavage site recognized by a protease found in cells to which the vaccine is intended to be administered and/or taken up and the fusion protein comprises multiple signal peptides linked to the N-terminus of each Consensus PF immunogens such that upon cleavage, the signal peptide of each Consensus PF immunogen translocates the respective Consensus PF immunogen to outside the cell.

(3) Bacterial Antigens

The antigen can be bacterial antigen or fragment or variant thereof. The bacterium can be from any one of the following phyla: Acidobacteria, Actinobacteria, Aquificae, Bacteroidetes, Caldiserica, Chlamydiae, Chlorobi, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia.

The bacterium can be a gram positive bacterium or a gram negative bacterium. The bacterium can be an aerobic bacterium or an anerobic bacterium. The bacterium can be an autotrophic bacterium or a heterotrophic bacterium. The bacterium can be a mesophile, a neutrophile, an extremophile, an acidophile, an alkaliphile, a thermophile, psychrophile, halophile, or an osmophile.

The bacterium can be an anthrax bacterium, an antibiotic resistant bacterium, a disease causing bacterium, a food poisoning bacterium, an infectious bacterium, *Salmonella* bacterium, *Staphylococcus* bacterium, *Streptococcus* bacterium, or tetanus bacterium. The bacterium can be a mycobacteria, *Clostridium tetani, Yersinia pestis, Bacillus anthracis*, methicillin-resistant *Staphylococcus aureus* (MRSA), or *Clostridium difficile*.

(a) *Mycobacterium tuberculosis* Antigens

IL-23 can be associated or combined with a *Mycobacterium tuberculosis* antigen (i.e., TB antigen or TB immunogen), or fragment thereof, or variant thereof. The TB antigen can be from the Ag85 family of TB antigens, for example, Ag85A and Ag85B. The TB antigen can be from the Esx family of TB antigens, for example, EsxA, EsxB, EsxC, EsxD, EsxE, EsxF, EsxH, EsxO, EsxQ, EsxR, EsxS, EsxT, EsxU, EsxV, and EsxW.

In some embodiments, the TB antigen can be heterologous nucleic acid molecules such as plasmids, which encode one or more of the *Mycobacterium tuberculosis* immunogens from the Ag85 family and the Esx family. The immunogens can be full-length or immunogenic fragments of full-length proteins. The immunogens can comprise consensus sequences and/or modifications for improved expression. Consensus immunogens may comprise a signal peptide such as an immunoglobulin signal peptide such as an IgE or IgG signal peptide and in some embodiments, may comprise an HA tag.

(4) Fungal Antigens

The antigen can be a fungal antigen or fragment or variant thereof. The fungus can be *Aspergillus* species, *Blastomyces dermatitidis, Candida* yeasts (e.g., *Candida albicans*), *Coccidioides, Cryptococcus neoformans, Cryptococcus gattii*, dermatophyte, *Fusarium* species, *Histoplasma capsulatum*, Mucoromycotina, *Pneumocystis jirovecii, Sporothrix schenckii, Exserohilum*, or *Cladosporium*.

c. Vector

The vaccine can comprise one or more vectors that include one or more heterologous nucleic acids encoding the antigen and the adjuvant. The one or more vectors can be capable of expressing the antigen and the adjuvant. The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vectors

The vector can be a circular plasmid or a linear nucleic acid. The circular plasmid and linear nucleic acid are capable of directing expression of a particular heterologous nucleotide sequence in an appropriate subject cell. The vector can have a promoter operably linked to the antigen-encoding nucleotide sequence, or the adjuvant-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or an inducible promoter, which initiates transcription only when the host cell is exposed to some particular external stimulus. In the case of a multicellular organism, the promoter can also be specific to a particular tissue or organ or stage of development.

(2) Circular and Linear Vectors

The vector may be circular plasmid, which may transform a target cell by integration into the cellular genome or exist extrachromosomally (e.g. autonomous replicating plasmid with an origin of replication).

The vector can be pVAX, pcDNA3.0, or provax, or any other expression vector capable of expressing heterologous DNA encoding the antigen, or the adjuvant and enabling a cell to translate the sequence to an antigen that is recognized by the immune system, or the adjuvant.

Also provided herein is a linear nucleic acid vaccine, or linear expression cassette ("LEC"), that is capable of being efficiently delivered to a subject via electroporation and expressing one or more desired antigens, and/or one or more desired adjuvants. The LEC may be any linear DNA devoid of any phosphate backbone. The DNA may encode one or more antigens, and/or one or more adjuvants. The LEC may contain a promoter, an intron, a stop codon, and/or a polyadenylation signal. The expression of the antigen, or the adjuvant may be controlled by the promoter. The LEC may not contain any antibiotic resistance genes and/or a phosphate backbone. The LEC may not contain other nucleic acid sequences unrelated to the desired antigen gene expression, or the desired adjuvant expression.

Figure 1B:
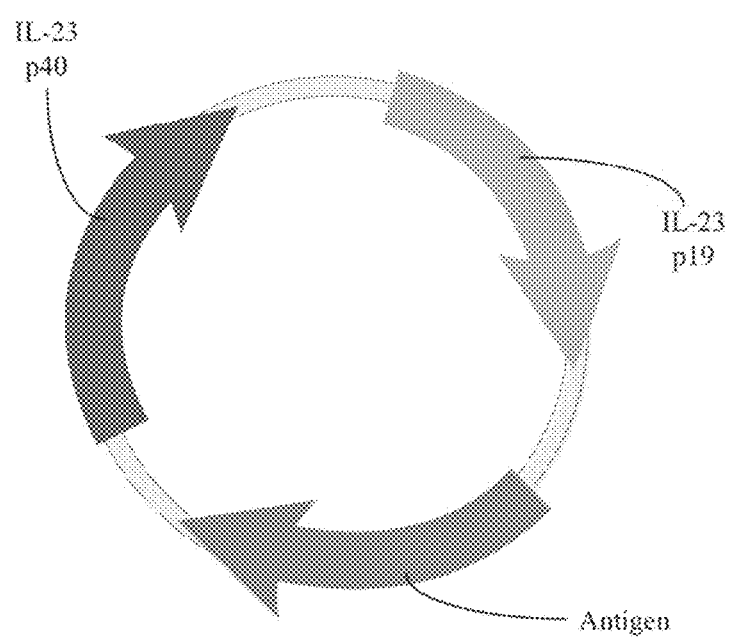

The p19 subunit of IL-23, the p40 subunit of IL-23, and/or the antigen can be arranged in a plasmid together or separately. By way of example only, some arrangements are shown schematically in FIGS. 1A and 1B.

The LEC may be derived from any plasmid capable of being linearized. The plasmid may be capable of expressing the antigen, and/or the adjuvant. The plasmid may be capable of expressing the adjuvant IL-23, for example, as a dual promoter plasmid having the p19 subunit under the control of a first promoter and the p40 subunit under the control of a second promoter. The first and second promoters may or may not be the same promoters. The plasmid may be WLV009-mIL-23 Opt (SEQ ID NO:13) as shown in FIG. 2. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen, or encoding the adjuvant, and enabling a cell to translate the sequence to an antigen that is recognized by the immune system, or the adjuvant.

The LEC can be pcrM2. The LEC can be pcrNP. pcrNP and pcrMR can be derived from pNP (Puerto Rico/34) and pM2 (New Caledonia/99), respectively.

(3) Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence, or the adjuvant sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination. The promoter may be operably linked to the nucleic acid sequence encoding the adjuvant and signals required for efficient polyadenylation of the transcript, ribosome binding sites, and translation termination.

The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

d. Excipients and Other Components of the Vaccine

The vaccine may further comprise a pharmaceutically acceptable excipient. The pharmaceutically acceptable excipient can be functional molecules such as vehicles, adjuvants other than IL-23, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent can be a polyanion, polycation, including poly-L-glutamate (LGS), or lipid. The transfection facilitating agent can be poly-L-glutamate, and the poly-L-glutamate can be present in the vaccine at a concentration of less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene. Hyaluronic acid can also be used or administered in conjunction with the genetic construct. The DNA plasmid vaccines may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant in addition to IL-23. The additional adjuvant can be other genes that are expressed in an alternative plasmid or are delivered as proteins in combination with the plasmid above in the vaccine. The adjuvant may be selected from the group consisting of: $\alpha$-interferon (IFN-$\alpha$), $\beta$-interferon (IFN-$\beta$), $\gamma$-interferon, platelet derived growth factor (PDGF), TNF$\alpha$, TNF$\beta$, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNF$\alpha$, TNF$\beta$, GM-CSF, epidermal growth factor (EGF), IL-1, IL-2, IL-4, IL-5, IL-6, IL-10, IL-12, IL-18, or a combination thereof.

Other genes that can be useful as adjuvants in addition to IL-23 include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRCS, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Serial No. 021,579 filed Apr. 1, 1994, which is fully incorporated by reference.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

3. METHODS OF VACCINATION

The present invention is also directed to methods of increasing an immune response in a subject by different routes of administration of the vaccine. Increasing the immune response can be used to treat and/or prevent disease in the subject.

The method can include administering the herein disclosed vaccines to the subject. The subject administered the vaccine can have an increased or boosted immune response as compared to a subject administered the antigen alone. In some embodiments, the immune response in the subject administered the vaccine can be increased by about 18% to about 650%. Alternatively, the immune response in the subject administered the vaccine may be increased by about 45% to about 260%. In still other alternative embodiments, the immune response in the subject administered the vaccine may be increased by about 93% to about 130%.

In other embodiments, the administered vaccine can increase or boost the immune response in the subject by at least about 1.5-fold, at least about 2-fold, at least about 2.5-fold, at least about 3-fold, at least about 4-fold, at least about 5-fold, at least about 6-fold, at least about 7-fold, at least about 8-fold, at least about 9-fold, or at least about 10-fold.

The vaccine dose can be between 1 µg to 10 mg active component/kg body weight/time, and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

a. Administration

The vaccine can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a horse, a cow, a pig, a sheep, a cat, a dog, a rat, or a mouse.

The vaccine can be administered prophylactically or therapeutically. In prophylactic administration, the vaccines can be administered in an amount sufficient to induce an immune response. In therapeutic applications, the vaccines are administered to a subject in need thereof in an amount sufficient to elicit a therapeutic effect. An amount adequate to accomplish this is defined as "therapeutically effective dose." Amounts effective for this use will depend on, e.g., the particular composition of the vaccine regimen administered, the manner of administration, the stage and severity of the disease, the general state of health of the patient, and the judgment of the prescribing physician.

The vaccine can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the vaccine can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The vaccines can be delivered via a variety of routes. Typical delivery routes include parenteral administration, e.g., intradermal, intramuscular or subcutaneous delivery. Other routes include oral administration, intranasal, and intravaginal routes. For the DNA of the vaccine in particular, the vaccine can be delivered to the interstitial spaces of tissues of an individual (Felgner et al., U.S. Pat. Nos. 5,580,859 and 5,703,055, the contents of all of which are incorporated herein by reference in their entirety). The vaccine can also be administered to muscle, or can be administered via intradermal or subcutaneous injections, or transdermally, such as by iontophoresis. Epidermal administration of the vaccine can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The vaccine can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

The vaccine can be a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

The vaccine can be incorporated into liposomes, microspheres or other polymer matrices (Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the vaccine described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the vaccine into tissue without the use of a needle. The MID may inject the vaccine as a small stream or jet with such force that the vaccine pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. No. 6,520,950; U.S. Pat. No. 7,171,264; U.S. Pat. No. 6,208,893; U.S. Pat. No. 6,009,347; U.S. Pat. No. 6,120,493; U.S. Pat. No. 7,245,963; U.S. Pat. No. 7,328,064; and U.S. Pat. No. 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired vaccine in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver vaccines to all types of tissues, particularly to skin and mucosa. In some embodiments, a needle-free injector may be used to propel a liquid that contains the vaccine to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example, set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle vaccine injectors that deliver the vaccine and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA (Inovio Pharmaceuticals, Blue Bell Pa.) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The Cellectra device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described vaccine herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired, means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could, for example, be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprises means for applying a voltage to the needle. This allows the needle to be used not only for injection but also as an electrode during electroporation. This is particularly advantageous as it means that the electric field is applied to the same area as the injected fluid. There has traditionally been a problem with electroporation in that it is very difficult to accurately align an electrode with previously injected fluid and so user's have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

The present invention has multiple aspects, illustrated by the following non-limiting examples.

3. EXAMPLES

Example 1

Expression of IL-23

A plasmid (i.e., WLV009-mIL-23 Opt) encoding the p19 and p40 subunits or chains of mouse IL-23 was constructed for expression of IL-23 (FIG. 2). The DNA sequences of p19 and p40 were codon and RNA optimized before insertion into the plasmid. p19 and p40 are under the control of separate promoters. Specifically, the nucleic acid sequence encoding optimized mouse p19 is located at nucleotides 3199-2549 of WLV009-mIL-23 Opt (SEQ ID NO:13; FIG. 2) and the sense strand of the nucleic acid sequence encoding optimized mouse p19 is shown in SEQ ID NO:18. The nucleic acid sequence encoding optimized mouse p40 is located at nucleotides 5034-6101 of WLV009-mIL-23 Opt (SEQ ID NO:13; FIG. 2) and the sense strand of the nucleic acid sequence encoding optimized p40 is shown in SEQ ID NO:20. Note that expression of p19 and p40 was driven in opposite directions on the WLV009-mIL-23 Opt plasmid (FIG. 2).

Figure 3:
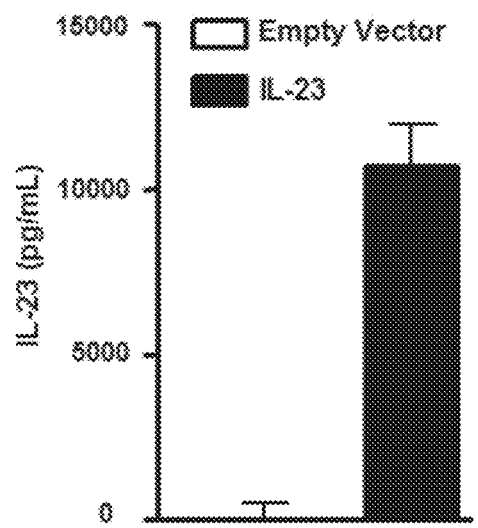
FIG. 3 shows expression of IL-23 in supernatants from transfected HEK 293T cells.

The plasmid was transfected into HEK 293T cells to confirm IL-23 expression. Cell supernatants were analyzed by ELISA. The results showed that the IL-23 p19/p40 heterodimer was expressed in the HEK 293T cells (FIG. 3).

Example 2

Intramuscular Immunization

Mice were used as a model system to determine whether IL-23 could function as an adjuvant when the vaccine was administered via an intramuscular route. The vaccine included a human papilloma virus (HPV) antigen and IL-23, both of which were encoded by respective plasmids.

The HPV antigen includes the HPV genotype 16 E6 and E7 antigens (HPV16 E6 and E7 antigens) in combination with an IgE leader sequence. The 818 nucleotide DNA sequence of the HPV antigen was as follows, in which the DNA corresponding to the IgE sequence is shown by underline:

```
                                             (SEQ ID NO: 16)
gaattcgccaccatggactggacctggatcctgttcctggtggccgccg ccacacgggtgcacagcttccaggaccccaggagagcggcagaaagct gcctcagctgtgtaccgagctgcagaccaccatccacgacatcatcctg gagtgtgtgtactgtaagcagcagctgctgaggagagaggtgtacgacc gggacctgtgtatcgtgtacagggacggcaatccctacgccgtgtgtga caagtgcctgaagttctacagcaagatcagcgagtaccggcactactgc tacagcctgtacggcaccaccctggagcagcagtacaacaagcccctgt gtgacctgctgatccggtgtatcaactgccagaagcccctgcagagaca
```

-continued
```
cctggacaagaagcagcggttccacaacatcaggggcagatggaccggc agatgtatgagctgctgccggagcagcagaaccagaagggagacccagc tgagaggccggaagagaagaagccacggcgatacccccaccctgcacga gtacatgctggacctgcagcctgagaccaccgatctgtacggctacggc cagctgaatgacagcagcgaggaggaggatgagatcgacggccctgccg gccaggccgagcccgacagagcccactacaacatcgtgaccttttgctg taagtgtgacagcaccctgagactgtgcgtgcagagcaccacgtggac atcagaaccctggaggatctgctgatgggcaccctgggcatcgtgtgtc ccatctgctcccagaaaccctgatgagcggccgc
```

The amino acid sequence of the HPV antigen was as follows, in which the amino acid sequence corresponding the IgE sequence is shown by underline:

```
                                        (SEQ ID NO: 17)
Met Asp Trp Thr Trp Ile Leu Phe Leu Val Ala Ala

Ala Thr Arg Val His Ser Phe Gln Asp Pro Gln Glu

Ser Gly Arg Lys Leu Pro Gln Leu Cys Thr Glu Leu

Gln Thr Thr Ile His Asp Ile Ile Leu Glu Cys Val

Tyr Cys Lys Gln Gln Leu Leu Arg Arg Glu Val Tyr

Asp Arg Asp Leu Cys Ile Val Tyr Arg Asp Gly Asn

Pro Tyr Ala Val Cys Asp Lys Cys Leu Lys Phe Tyr

Ser Lys Ile Ser Glu Tyr Arg His Tyr Cys Tyr Ser

Leu Tyr Gly Thr Thr Leu Glu Gln Gln Tyr Asn Lys

Pro Leu Cys Asp Leu Leu Ile Arg Cys Ile Asn Cys

Gln Lys Pro Leu Gln Arg His Leu Asp Lys Lys Gln

Arg Phe His Asn Ile Arg Gly Arg Trp Thr Gly Arg

Cys Met Ser Cys Cys Arg Ser Ser Arg Thr Arg Arg

Glu Thr Gln Leu Arg Gly Arg Lys Arg Arg Ser His

Gly Asp Thr Pro Thr Leu His Glu Tyr Met Leu Asp

Leu Gln Pro Glu Thr Thr Asp Leu Tyr Gly Tyr Gly

Gln Leu Asn Asp Ser Ser Glu Glu Glu Asp Glu Ile

Asp Gly Pro Ala Gly Gln Ala Glu Pro Asp Arg Ala

His Tyr Asn Ile Val Thr Phe Cys Cys Lys Cys Asp

Ser Thr Leu Arg Leu Cys Val Gln Ser Thr His Val

Asp Ile Arg Thr Leu Glu Asp Leu Leu Met Gly Thr

Leu Gly Ile Val Cys Pro Ile Cys Ser Gln Lys Pro
```

Specifically, a group of mice were immunized with the plasmid WLV009-mIL-23 Opt (FIG. 2 and described above in Example 1) and a plasmid encoding the HPV16 E6 and E7 antigens as described above. A second group of mice were immunized only with the plasmid encoding the HPV16 E6 and E7 antigens. Mice were immunized by the intramuscular route using electroporation. An Interferon Gamma ELISpot assay was used to examine the cellular immune response in the immunized groups of mice.

Figure 4:
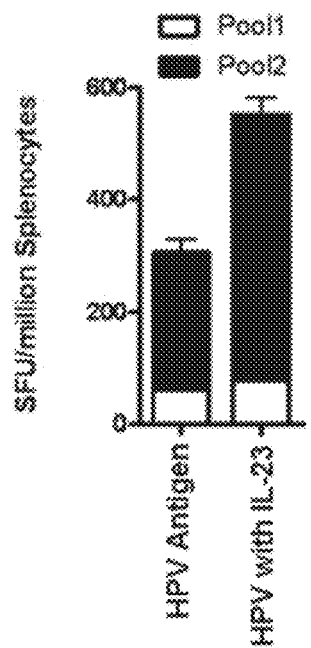
FIG. 4 shows the cellular immune response in mice immunized via an intramuscular route.

As shown in FIG. 4, the presence of IL-23 predominately increased the cellular immune response to the HPV16 E7 antigen (i.e., pool 2) as compared to the antigen alone. Particularly, IL-23 increased the cellular immune response by about 2-fold. Pool 2 includes the full sequence of the E7 antigen, and pool 1 includes the full sequence of the E6 antigen.

Figure 5:
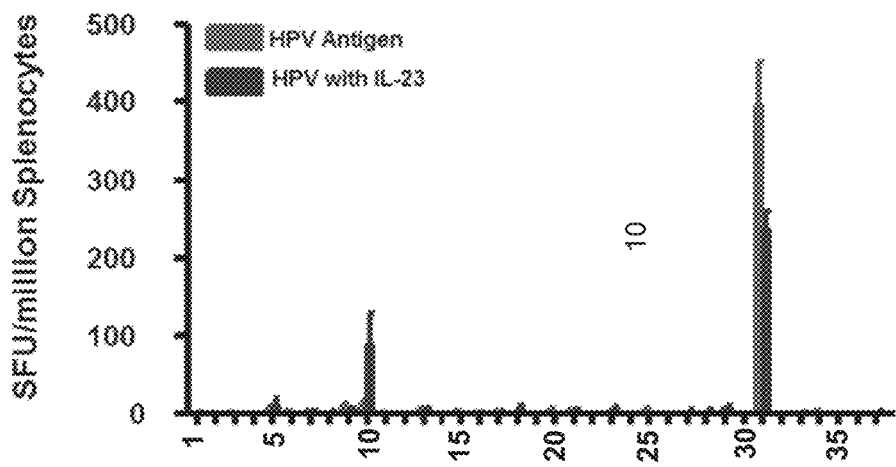
FIG. 5 shows epitope recognition of the human papilloma virus (HPV) antigen by the immune system in mice immunized with and without a nucleic acid encoding IL-23.
Figure 6:
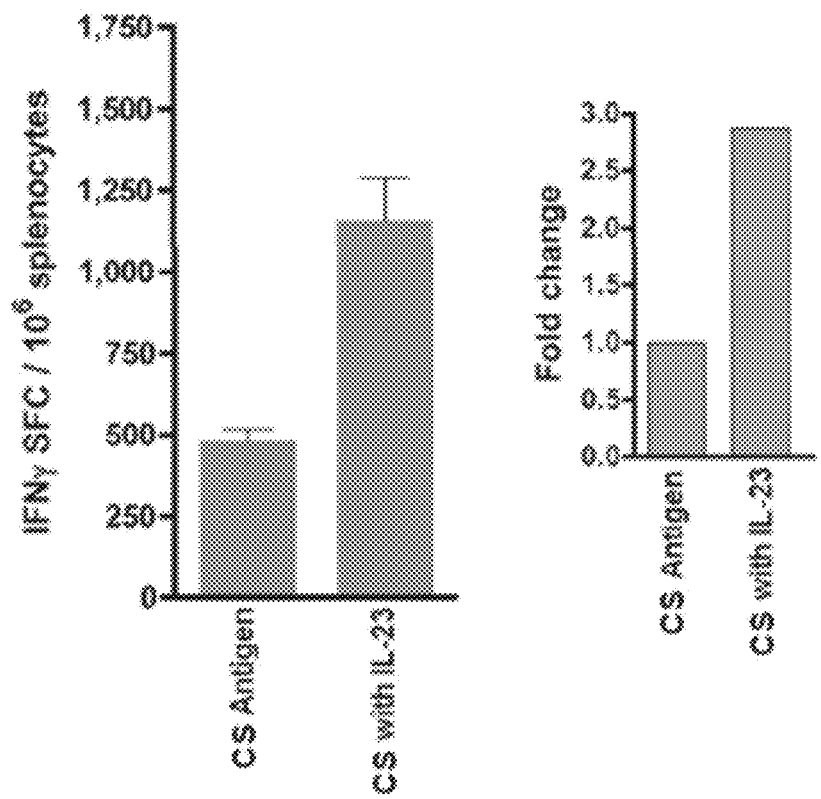
FIG. 6 shows the cellular immune response in mice immunized via an intradermal route.

To further examine the increased cellular immune response, epitopes within the antigen were fine mapped using the Interferon Gamma ELISpot assay (FIG. 5). Immunization with the plasmid encoding the HPV16 E6 and E7 antigens alone resulted in recognition of single epitope (i.e., epitope 31). Immunization, however, with the plasmid WLV009-mIL-23 Opt and the plasmid encoding the HPV16 E6 and E7 antigens resulted in recognition of an additional epitope (i.e., epitope 10). Taken together, these data indicated that IL-23 has the ability to augment the cellular immune response and alter epitope presentation in muscle tissue.

The above data showed that IL-23 has the ability to function as an adjuvant when administered by an intramuscular route because IL-23 augmented the cellular immune response to the HPV antigen. The above data also indicated that IL-23 is able to function as an adjuvant with a viral antigen. The above data also unexpectedly showed that IL-23 altered the recognition of an epitope in the HPV antigen.

Example 3

Intradermal Immunization

Mice were used as a model system to determine whether IL-23 could function as an adjuvant when the vaccine was administered via an intradermal route. The vaccine included a circumsporozoite (CS) antigen from the parasite *Plasmodium falciparum* and IL-23. The CS antigen and IL-23 were encoded by separate plasmids.

The CS antigen includes a consensus CS immunogen having the 1239 nucleotide DNA sequence shown below:

```
                                        (SEQ ID NO: 14)
atgatgcggaagaggctatcctgagcgtgtccagatcctgttcgtggagg ccctgttccaagagtaccagtgctacggcagcagcagcaacacaagagtg ctgaacgagagaactacgacaacgccggcaccaacctgtacaacgagagg aaatgaactactacggcaagcaggaaaactggtacagcctgaagaagaac agccggtcctgggcgagaacgacgacggcaacaacaacaacggcgacaa cggcagagagggcaaggacgaggacaagcgggatggcaacaacgaggaca acgagaagctgcggaagcccaagcacaagaagctgaagcagcccggcgac ggcaaccccgaccccaacgccaacccaacgtggaccccaatgccaatcc taatgtcgatcccaacgctaacccaaatgtcgacctaacgcaaatccta acgccaatcccaatgcaaaccctaatgccaacccaaatgctaatccaaac gcaaaccccaatgctaaccccaacgctaaccctaatgcaaatccaaatgc caaccccaacgccaacccaaacgccaatcccaacgctaatcctaacgcta accccaacgccaatcctaacgccaacccaaacgctaacccaaatgccaac cccaatgcaaatcctaatgctaatcctaacgctaatccaaatgcaaatcc aaacgctaatcctaatgccaaccctaacgcaaaccccaacgcaaatccaa atgctaacccaaatgcaaatcccaacgccaatccaaacgcaaatccaaat
```

-continued

```
gccaatcctaatgcaaaccctaatgcaaatcccaatgctaatcctaatgc taatccaaacaagaacaaccagggcaacggccagggccacaacatgccca acgacccaaccggaacgtggacgagaatgccaatgccaacaacgccgtg aagaacaacaacaatgaggaacccagcgacaagcacatcgagcagtacct caagaagatccagaacagcctgagcaccgagtggagccctgtagcgtga cctgcggcaacggcatccaagtccggatcaagcccggcagcgccaacaag cccaaggacgagctggattacgagaacgacatcgagaagaaaatctgcaa gatggaaaagtgcagcagcgtgttcaacgtggtcaacagcagcatcggcc tgatcatggtgctgagctttctgttcctcaactga
```

The corresponding amino acid sequence for the CS antigen is shown below, having a length of 412 amino acids:

(SEQ ID NO: 15)

```
Met Met Arg Lys Leu Ala Ile Leu Ser Val Ser Ser

Phe Leu Phe Val Glu Ala Leu Phe Gln Glu Tyr Gln

Cys Tyr Gly Ser Ser Ser Asn Thr Arg Val Leu Asn

Glu Leu Asn Tyr Asp Asn Ala Gly Thr Asn Leu Tyr

Asn Glu Leu Glu Met Asn Tyr Tyr Gly Lys Gln Glu

Asn Trp Tyr Ser Leu Lys Lys Asn Ser Arg Ser Leu

Gly Glu Asn Asp Asp Gly Asn Asn Asn Gly Asp

Asn Gly Arg Glu Gly Lys Asp Glu Asp Lys Arg Asp

Gly Asn Asn Glu Asp Asn Glu Lys Leu Arg Lys Pro

Lys His Lys Lys Leu Lys Gln Pro Gly Asp Gly Asn

Pro Asp Pro Asn Ala Asn Pro Asn Val Asp Pro Asn

Ala Asn Pro Asn Val Asp Pro Asn Ala Asn Pro Asn

Val Asp Pro Asn Ala Asn Pro Asn Ala Asn Pro Asn

Ala Asn Pro Asn Ala Asn Pro Asn Ala Asn Pro Asn

Ala Asn Pro Asn Ala Asn Pro Asn Ala Asn Pro Asn

Ala Asn Pro Asn Ala Asn Pro Asn Ala Asn Pro Asn

Ala Asn Pro Asn Ala Asn Pro Asn Ala Asn Pro Asn

Ala Asn Pro Asn Ala Asn Pro Asn Ala Asn Pro Asn

Ala Asn Pro Asn Ala Asn Pro Asn Ala Asn Pro Asn

Ala Asn Pro Asn Ala Asn Pro Asn Ala Asn Pro Asn

Ala Asn Pro Asn Ala Asn Pro Asn Ala Asn Pro Asn

Ala Asn Pro Asn Ala Asn Pro Asn Ala Asn Pro Asn

Ala Asn Pro Asn Ala Asn Pro Asn Ala Asn Pro Asn

Lys Asn Asn Gln Gly Asn Gly Gln Gly His Asn Met

Pro Asn Asp Pro Asn Arg Asn Val Asp Glu Asn Ala

Asn Ala Asn Asn Ala Val Lys Asn Asn Asn Asn Glu

Glu Pro Ser Asp Lys His Ile Glu Gln Tyr Leu Lys

Lys Ile Gln Asn Ser Leu Ser Thr Glu Trp Ser Pro

Cys Ser Val Thr Cys Gly Asn Gly Ile Gln Val Arg

Ile Lys Pro Gly Ser Ala Asn Lys Pro Lys Asp Glu

Leu Asp Tyr Glu Asn Asp Ile Glu Lys Lys Ile Cys

Lys Met Glu Lys Cys Ser Ser Val Phe Asn Val Val

Asn Ser Ser Ile Gly Leu Ile Met Val Leu Ser Phe

Leu Phe Leu Asn
```

Specifically, a group of mice were immunized with the plasmid WLV009-mIL-23 Opt (FIG. 2 and described above in Example 1) and a plasmid encoding the CS antigen as described above. A second group of mice were immunized only with the plasmid encoding the CS antigen. Mice were immunized via an intradermal route using electroporation. An Interferon Gamma ELISpot assay was used to examine the cellular immune response in the immunized groups of mice.

As shown in FIG. 6, the presence of IL-23 increased the cellular immune response by greater than 2-fold to the CS antigen as compared to antigen alone. Particularly, IL-23 increased the cellular immune response by about 3-fold. Accordingly, these data indicated that IL-23 is able to function as an adjuvant in skin tissue because IL-23 augmented the cellular immune response to the CS antigen. These data also indicated that IL-23 is able to function as an adjuvant with a parasite antigen.

The above data from the intradermal and intramuscular immunizations showed that IL-23 has the surprising ability to function as an adjuvant when administered by intramuscular and intradermal routes. IL-23 augmented the cellular immune response in muscle and skin tissues irrespective of the identity or source of the antigen.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A vaccine comprising one or more nucleic acid sequences that encode an antigen and Interleukin-23 (IL-23) comprising p19 subunit and p40 subunit, wherein p19 subunit of IL-23 is encoded by a nucleic acid that is 95% identical or greater to the nucleotide sequence as set forth in SEQ ID NO:22 and wherein p40 subunit of IL-23 is encoded by a nucleic acid that is 95% identical or greater to the nucleotide sequence as set forth in SEQ ID NO:23.

2. The vaccine of claim 1, wherein p19 subunit of IL-23 is encoded by the nucleotide sequence as set forth in SEQ ID NO:22 and p40 subunit of IL-23 is encoded by the nucleotide sequence as set forth in SEQ ID NO:23.

3. The vaccine of claim 1, wherein the antigen is encoded by a first nucleic acid and IL-23 is encoded by a second nucleic acid.

4. The vaccine of claim 3, comprising an antigen peptide encoded by the first nucleic acid and an IL-23 peptide encoded by the second nucleic acid.

5. The vaccine of claim 1, wherein the antigen is selected from a group consisting of a human papilloma virus (HPV) antigen, an HIV antigen, an influenza antigen, a *Plasmodium falciparum* antigen and a fragment thereof.

6. The vaccine of claim 5, wherein the HPV antigen is selected from the group consisting of HPV16 E6 antigen, an HPV16 E7 antigen and a combination thereof; wherein the HIV antigen is selected from the group consisting of Env A, Env B, Env C, Env D, B Nef-Rev, Gag, and any combination thereof; wherein the influenza antigen is selected from the group consisting of H1 HA, H2 HA, H3 HA, H5 HA, BHA antigen and any combination thereof; and wherein the *Plasmodium falciparum* antigen is a circumsporozoite (CS) antigen.

7. The vaccine of claim 1, further comprising a pharmaceutically acceptable excipient.

8. The vaccine of claim 3, wherein the second nucleic acid further comprises an expression vector.

9. A method for increasing an immune response in a subject, the method comprising administering the vaccine of claim 1 to the subject in need thereof.

10. The method of claim 9, wherein administering the vaccine includes at least one of intramuscular administration and intradermal administration.

11. The method of claim 9, wherein administering the vaccine includes electroporation.

12. The method of claim 9, wherein the increased immune response occurs in at least one of a skin tissue and a muscle tissue of the subject.

13. The method of claim 9, wherein the immune response in the subject is increased by about 75% to about 200%.

14. The method of claim 13, wherein the immune response in the subject is increased by about 90% to about 130%.

15. The method of claim 13, wherein the immune response in the subject is increased by about 105%.

16. The method of claim 9, wherein the immune response in the subject is increased by at least about 3-fold.

17. The method of claim 9, wherein the immune response in the subject is increased by at least about 1.5 fold.

18. The method of claim 9, further comprising altering recognition of at least one epitope in the antigen.

19. The method of claim 18, wherein the at least one epitope in the antigen failed to be recognized by an immune system of a subject administered the antigen alone.

20. The method of claim 18, wherein the antigen is a human papilloma virus (HPV) antigen.

21. A nucleic acid molecule comprising one or more nucleotide sequences selected from the group consisting of: 1) SEQ ID NO: 22, 2) a nucleotide sequence that is 95% identical or greater to SEQ ID NO:22, 3) a nucleotide sequence that encodes IL-23, wherein p19 subunit of IL-23 is encoded by a nucleotide sequence that is 95% identical or greater to the nucleotide sequence as set forth in SEQ ID NO:22 and wherein p40 subunit of IL-23 is encoded by a nucleotide sequence that is 95% identical or greater to the nucleotide sequence as set forth in SEQ ID NO:23.

22. The nucleic acid molecule of claim 21, wherein the nucleic acid molecule is comprised of one or more plasmids.

* * * * *